(12) United States Patent
Gudibande et al.

(10) Patent No.: US 12,298,215 B2
(45) Date of Patent: May 13, 2025

(54) POLAR FLUID GATED FIELD EFFECT DEVICES

(71) Applicant: GRAPHWEAR TECHNOLOGIES INC., San Francisco, CA (US)

(72) Inventors: Rajatesh Ravindra Gudibande, San Francisco, CA (US); Saurabh Radhakrishnan, San Francisco, CA (US); Antoine Galand, San Francisco, CA (US); Meet Vora, San Francisco, CA (US)

(73) Assignee: GRAPHWEAR TECHNOLOGIES INC., San Francisco, CA (US)

( * ) Notice: Subject to any disclaimer, the term of this patent is extended or adjusted under 35 U.S.C. 154(b) by 899 days.

(21) Appl. No.: 16/221,384

(22) Filed: Dec. 14, 2018

(65) Prior Publication Data

US 2019/0257732 A1    Aug. 22, 2019

Related U.S. Application Data

(63) Continuation of application No. PCT/IB2017/001003, filed on Jun. 30, 2017.

(60) Provisional application No. 62/356,742, filed on Jun. 30, 2016, provisional application No. 62/356,729, (Continued)

(51) Int. Cl.
| | |
|---|---|
| *G01N 15/06* | (2024.01) |
| *B82Y 15/00* | (2011.01) |
| *B82Y 30/00* | (2011.01) |
| *G01N 27/414* | (2006.01) |

(Continued)

(52) U.S. Cl.
CPC ..... *G01N 15/0656* (2013.01); *G01N 27/4145* (2013.01); *G01N 27/4146* (2013.01); *G01N 33/54373* (2013.01); *G01N 33/5438* (2013.01); *G01N 33/6845* (2013.01);
(Continued)

(58) Field of Classification Search
CPC .......... G01N 15/0656; G01N 27/4145; G01N 27/4146; G01N 33/54373; G01N 33/5438; G01N 33/6845; B82Y 15/00; B82Y 30/00
See application file for complete search history.

(56) References Cited

U.S. PATENT DOCUMENTS

| | | |
|---|---|---|
| 8,716,029 B1 | 5/2014 | Kim et al. |
| 9,214,559 B2 | 12/2015 | Lee et al. |
| 9,592,007 B2 | 3/2017 | Nuovo et al. |

(Continued)

FOREIGN PATENT DOCUMENTS

| | | | | |
|---|---|---|---|---|
| JP | 2012088326 A | 5/2012 | | |
| WO | WO-2008066458 A1 * | 6/2008 | .......... | D03D 1/0088 |

(Continued)

OTHER PUBLICATIONS

Wang, B. et al. (2022) "Wearable aptamer-field-effect transistor sensing system for noninvasive cortisol monitoring." Sci. Adv. 8:1-15. (Year: 2022).*

(Continued)

*Primary Examiner* — Jill A Warden
*Assistant Examiner* — Jacqueline Brazin
(74) *Attorney, Agent, or Firm* — Shumaker, Loop & Kendrick, LLP

(57) ABSTRACT

Disclosed herein are nanoscale field effect transistors (NFETs), e.g., graphene based field effect transistors (GFETs), that do not have physical gates. Instead, they are gated by polar fluids. Systems and methods using such transistors are also disclosed.

25 Claims, 23 Drawing Sheets

| 1 Substrate | 2 Source | 3 Drain |
|---|---|---|
| 4 Receptor | 5 Graphene | 6 Back Polymer |

Gateless device with back polymer and receptor

Related U.S. Application Data filed on Jun. 30, 2016, provisional application No. 62/351,942, filed on Jun. 18, 2016.

(51) Int. Cl.
    *G01N 33/543*     (2006.01)
    *G01N 33/68*     (2006.01)

(52) U.S. Cl.
    CPC ........... *A61B 2562/00* (2013.01); *B82Y 15/00* (2013.01); *B82Y 30/00* (2013.01)

(56) References Cited

U.S. PATENT DOCUMENTS

| | | | |
|---|---|---|---|
| 9,954,309 B2 | 4/2018 | Eid et al. | |
| 10,722,160 B2 | 7/2020 | Wang et al. | |
| 2007/0096165 A1* | 5/2007 | Lipisko | G01N 27/4148 257/253 |
| 2007/0231211 A1 | 10/2007 | Yoo et al. | |
| 2008/0035494 A1 | 2/2008 | Gomez et al. | |
| 2010/0163283 A1* | 7/2010 | Hamedi | D03D 15/507 174/254 |
| 2013/0041235 A1* | 2/2013 | Rogers | H05K 1/0283 600/386 |
| 2013/0052632 A1* | 2/2013 | Carter | G01N 25/20 435/7.1 |
| 2015/0307936 A1 | 10/2015 | Goldsmith et al. | |
| 2015/0364018 A1* | 12/2015 | Mirov | G08B 6/00 340/407.1 |
| 2016/0178569 A1 | 6/2016 | Hoffman et al. | |
| 2016/0252517 A1* | 9/2016 | Lo | B01L 3/502738 506/9 |
| 2018/0059051 A1* | 3/2018 | Yang | G01N 33/552 |
| 2018/0263539 A1 | 9/2018 | Javey et al. | |
| 2019/0187148 A1 | 6/2019 | Lo et al. | |

FOREIGN PATENT DOCUMENTS

| | | | | |
|---|---|---|---|---|
| WO | WO-2010005738 A1 * | 1/2010 | | G01N 27/4148 |
| WO | WO-2014042660 A1 * | 3/2014 | | B82Y 30/00 |
| WO | WO-2015054663 A2 | 4/2015 | | |
| WO | WO-2015200758 A2 | 12/2015 | | |
| WO | WO-2017216641 A2 | 12/2017 | | |
| WO | WO-2019108366 A1 | 6/2019 | | |

OTHER PUBLICATIONS

Hodge-Miller, A. et al. (2003). "Gateless Depletion Mode Field Effect Transistor for Macromolecule Sensing". IEEE Proceedings 918-921. (Year: 2003).*
EP17812823.7 The Extended European Search Report dated Jan. 16, 2020.
Kam, et al. Polar Organic Gate Dielectrics for Graphene Field-Effect Transistor-Based Sensor Technology. Sensors (Basel). Aug. 23, 2018;18(9). pii: E2774. doi: 10.3390/s18092774.
He, et al. Solution-gated graphene field effect transistors integrated in microfluidic systems and used for flow velocity detection. Nano Lett. Mar. 14, 2012;12(3):1404-9. doi: 10.1021/nl2040805. Epub Feb. 14, 2012.
Ohno, et al. Electrolyte-gated graphene field-effect transistors for detecting pH and protein adsorption. Nano Lett. Sep. 2009;9(9):3318-22. doi: 10.1021/nl901596m.
PCT/IB17/01003 International Search Report dated Dec. 28, 2017.
PCT/IB17/01003 International Preliminary Report on Patentability dated Dec. 18, 2018.
Karimi, et al. Development of solution-gated graphene transistor model for biosensors, Nanoscale Research Letters. 9(2014).
Wang, X. et al. An aptameric graphene nanosensor for analyte detection in serum. 2016 IEEE 29th International Conference on Micro Electro Mechanical Systems (MEMS). (2016): 286-289.
Qi, Z.J. et al. Electronic Transport in Heterostructures of Chemical Vapor Deposited Graphene and Hexagonal Boron Nitride. Small, 11 (2015): 1402-1408.
Giannazzo, Filippo et al. Ambipolar MoS2 Transistors by Nanoscale Tailoring of Schottky Barrier Using Oxygen Plasma Functionalization. ACS applied materials & interfaces vol. 9,27 (2017): 23164-23174. doi:10.1021/acsami.7b04919.
Jacoby, Mitch. 2-D materials go beyond graphene. Vol. 95, 22 (2017).
Mir, Showkat Hassan et al. Recent advances in the carrier mobility of two-dimensional materials: a theoretical perspective. ACS omega 5.24 (2020): 14203-14211.
Thomas, Liji. Materials with Similar Properties of Graphene (2019).
Vargas-Bernal, Rafael. Graphene against Other Two-Dimensional Materials: A Comparative Study on the Basis of Photonic Applications (2016).

* cited by examiner

| 1 Substrate | 2 Source | 3 Drain |
| 4 Receptor | 5 Graphene | 6 Back Polymer |

Gateless device with back polymer and receptor

Gateless device with receptor but without back polymer

Gateless device with back polymer without receptor

Gateless device without back polymer or receptor

POLAR FLUID GATED FIELD EFFECT DEVICES

CROSS-REFERENCE

This application is a continuation application of International Application No. PCT/IB2017/001003, filed on Jun. 30, 2017 entitled "POLAR FLUID GATED FIELD EFFECT DEVICES," which claims priority to U.S. Provisional Patent Application No. 62/356,729, filed Jun. 30, 2016 and entitled "DETECTION OF IONIC CONCENTRATION IN FLUID USING NANOSCALE MATERIALS VIA A CAPACITIVE RESPONSE," and to U.S. Provisional Patent Application No. 62/356,742, filed Jun. 30, 2016 and entitled "LACTATE-OXIDASE-FUNCTIONALIZED GRAPHENE POLYMER COMPOSITES FOR LABEL-FREE DETECTION OF LACTATE IN SWEAT AND OTHER BODILY FLUIDS," and to U.S. Provisional Application No. 62/351,942, filed Jun. 18, 2016 entitled "BORONIC-ACID-FUNCTIONALIZED GRAPHEME POLYMER COMPOSITES FOR LABEL-FREE DETECTION OF GLUCOSE IN SWEAT AND OTHER BODILY FLUIDS," each of which is hereby incorporated by reference herein in its entirety.

FIELD OF THE INVENTION

The invention disclosed herein generally relates to the design, making and applications of nanoscale field effect transistors (NFETs) gated by polar fluids, in particular graphene field effect transistors (GFETs). The present disclosure also relates generally to chemical and biological sensing using field effect transistors and more particularly to bio-chemical sensing using field effect transistors with a bio-chemically sensitive channel involving graphene.

BACKGROUND OF THE INVENTION

The field-effect transistor (FET) is a transistor that uses an electric field to control the electrical behavior of the device. In general, a FET has three terminals (e.g., source, drain, and gate) and an active channel. Though the active channel, e.g., formed by a semi-conductive material, charge carriers (electrons or holes) flow from the source to the drain.

Source (S) is where the carriers enter the channel. Drain (D) is where the carriers leave the channel. Drain-to-source voltage is VDS, and source to drain current is IDS. Gate (G) modulates the channel conductivity by applying a gate voltage (VG) to control a current between source and drain.

Nanoscale field effect transistors (NFETs) such as graphene field effect transistors (GFETs) are widely used in numerous applications such as in bioprobes, implants, and etc.

What is needed in the field are better designs of FETs and new ways of using them.

SUMMARY OF THE INVENTION

In one aspect, disclosed herein is a field effect transistor. The field effect transistor comprises: a drain electrode; a drain electrode; a source electrode; an electrically insulating substrate; a nanoscale material layer arranged on the substrate, the nanoscale material layer partially defining an electrically conducting and chemically sensitive channel, the nanoscale material layer and the channel extending between and being electrically connected to the drain electrode and source electrode; and a polar fluid induced gate terminal created by a polar fluid exposed to the nanoscale material layer. In some embodiments, the polar fluid comprises the target analyte. In further embodiments, the polar fluid has a charge concentration sufficient to induce a polar fluid gate voltage that optimizes the gate voltage versus channel current characteristics of the field effect transistor in response to the target analyte.

In some embodiments, a constant current or a constant voltage is applied between the source and drain electrodes, provided by a constant current source or a constant voltage source.

In some embodiments, the nanoscale material comprises graphene, CNTs, MoS2, boron nitride, metal dichalcogenides, phosphorene, nanoparticles, quantum dots, fullerene, 2D nanoscale material, 3D nanoscale material, OD nanoscale material, 1D nanoscale material or any combination thereof.

In some embodiments, wherein the polar fluid comprises a solution with polar molecules, a gas with polar molecules, a target sensing analyte, or combinations thereof.

In some embodiments, the polar fluid comprises sweat, breath, saliva, earwax, urine, semen, blood plasma, a biofluid, a chemical fluid, an air sample, a gas sample, or a combination thereof.

In some embodiments, the target analyte comprises an electrolyte, glucose, lactic acid, IL6, a cytokine, HER2, cortisol, ZAG, cholesterol, vitamins, a protein, a drug molecule, a metabolite, a peptides, an amino acid, a DNA, an RNA, an aptamer, an enzyme, a biomolecule, a chemical molecule, a synthetic molecule, or combinations thereof.

In some embodiments, the field effect transistor, further comprises: a receptor layer deposited on the nanoscale material layer, wherein the receptor layer comprises receptors targeting the target analyte.

In some embodiments, the receptors comprise pyrene boronic acid (PBA), pyrene N-hydroxysuccinimide ester (Pyrene-NHS), organic chemicals, aromatic molecules, cyclic molecules, enzymes, proteins, antibodies, viruses, single stranded DNAs (ssDNAs), aptamers, inorganic materials, synthetic molecules, biological molecules.

In some embodiments, the field effect transistor, further comprises: a back polymer layer under the nanoscale material layer to provide support for additional mechanical, electrical, chemical, biological functionality or combinations thereof.

In some embodiments, the back polymer layer comprises: carbon polymers, bio polymers, PMMA, PDMS, flexible glass, nanoscale materials, silica gel, silicone, inks, printed polymers or any combination thereof.

In one aspect, disclosed herein is a method for sensing a target analyte in a polar fluid. The method comprises: exposing the polar fluid sample to a field effect transistor, where the field effect transistor comprises: a drain electrode; a source electrode; an electrically insulating substrate; a nanoscale material layer arranged on the substrate, the nanoscale material layer at least partially defining an electrically conducting and chemically sensitive channel, the nanoscale material layer and the channel extending between and being electrically connected to the drain electrode and source electrode; and a polar fluid induced gate terminal created by the polar fluid exposed to the nanoscale material layer, wherein the polar fluid comprises the target analyte and has charge concentration sufficient to induce a polar fluid gate voltage that optimize the gate voltage versus channel current characteristics of the field effect transistor for detecting the analyte; measuring a first source-drain voltage at a first time point and a second source-drain voltage at a second and subsequent time point; and determining a concentration of the target analyte in the polar fluid based on the first and second source-drain voltages.

In some embodiments, the nanoscale material comprises graphene, CNTs, MoS2, boron nitride, metal dichalcogenides, phosphorene, nanoparticles, quantum dots, fullerene, 2D nanoscale material, 3D nanoscale material, 0D nanoscale material, 1D nanoscale material or any combination thereof.

In some embodiments, the field effect transistor is functionalized with a receptor layer deposited on the nanoscale material layer, and wherein the receptor layer comprises receptors targeting the target analyte.

In some embodiments, the receptors comprise pyrene boronic acid (PBA), pyrene N-hydroxysuccinimide ester (Pyrene-NHS), organic chemicals, aromatic molecules, cyclic molecules, enzymes, proteins, antibodies, viruses, single stranded DNAs (ssDNAs), aptamers, inorganic materials, synthetic molecules, biological molecules.

In some embodiments, the target analyte comprises an electrolyte, glucose, lactic acid, IL6, a cytokine, HER2, cortisol, ZAG, cholesterol, vitamins, a protein, a drug molecule, a metabolite, a peptides, an amino acid, a DNA, an RNA, an aptamer, an enzyme, a biomolecule, a chemical molecule, a synthetic molecule, or combinations thereof.

In some embodiments, the polar fluid comprises a solution with polar molecules, gas with polar molecules, target sensing analyte or combinations thereof.

In some embodiments, the method further comprises calculating a fractional change between the first and second source-drain voltages.

In some embodiments, the method further comprises: applying a constant current between the source and drain electrodes of the field effect transistor.

In some embodiments, the method further comprises: applying a constant voltage between the source and drain electrodes of the field effect transistor.

In some embodiments, the polar fluid comprises sweat, breath, saliva, earwax, urine, semen, blood plasma, a biofluid, a chemical fluid, an air sample, a gas sample, or a combination thereof.

In some embodiments, the method further comprises: a back polymer layer under the nanoscale material layer to provide support for additional mechanical, electrical, chemical, biological functionality or combinations thereof.

In some embodiments, the back polymer layer comprises: carbon polymers, bio polymers, PMMA, PDMS, flexible glass, nanoscale materials, silica gel, silicone, inks, printed polymers or any combination thereof.

In one aspect, disclosed herein is a system comprising: a field effect transistor; and a constant current source or a constant voltage source electrically connected with the field effect transistor. The field effect transistor comprises: a drain electrode; a source electrode; an electrically insulating substrate; a nanoscale material layer arranged on the substrate, the nanoscale material layer partially defining an electrically conducting and chemically sensitive channel, the nanoscale material layer and the channel extending between and being electrically connected to the drain electrode and source electrode; and a polar fluid induced gate terminal created by a polar fluid exposed to the nanoscale material layer. In some embodiments, the polar fluid comprises the target analyte. In some embodiments, the polar fluid has a charge concentration sufficient to induce a polar fluid gate voltage that optimizes the gate voltage versus channel current characteristics of the field effect transistor in response to the target analyte.

In some embodiments, the constant current source maintains a constant current through the field effect transistor.

In some embodiments, the constant voltage source maintains a constant voltage over the field effect transistor.

In some embodiments, a voltage output or a current output is communicated, through a wired or wireless transmission, to a digital platform.

In some embodiments, the digital platform comprises a smart phone, a tablet computer, a smart watch, an in-car entertainment system, a laptop computer, desktop computers, a computer terminal, a television system, e-book reader, a wearable device, or any other type of computing device that processes digital input.

As known by one of skill in the art, any embodiments disclosed herein can be used in conjunction, solely or in combination with other embodiments, with any aspect of the invention.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Disclosed herein are nanoscale field effect transistors and methods of making and using the same.

Graphene Field Effect Transistors in General

Graphene possesses a remarkable mechanical resistance; this enables thicknesses on the order of a monolayer or bilayer to be subjected to a substantial mechanical stress without losing its primary electrical properties. Such mechanical strength makes graphene an ideal candidate to replace the current generation of transparent conductive oxides (TCO), led by Indium Tin Oxide (ITO). Unlike graphene, ITO is brittle and susceptible to mechanical stress; however its low sheet resistance and high transparency are enough to offset its high material costs. The production of large area and low sheet resistance graphene sheets, on the other hand, is a relatively straightforward and scalable process using chemical vapor deposition (CVD), yielding few atomic layers with transparency higher than 90% and sheet resistances lower than 100 after proper treatment.

Figure 1A:
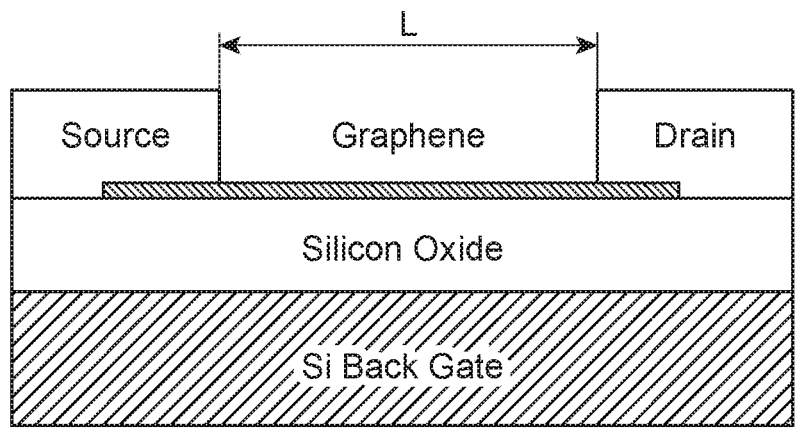
FIG. 1A depicts an embodiment of the prior art, illustrating a graphene field-effect transistor (gFET).

As depicted in FIG. 1A, Graphene FETs are generally fabricated on a Si wafer covered with a $SiO_2$ layer, and graphene forms the transistor channel. The graphene transistor consists of three terminals: source and drain metal electrodes contacting the graphene channel and a global back gate enabled by the doped Si substrate. These features facilitate the characteristic ambipolar transport behavior of graphene in the Grat-FETs—achieving both n-type and p-type transport when biased with a proper gate voltage at the substrate. Any applicable method can be applied to fabricate a GFET, including, for example, the information disclosed in International Patent Publication No. WO 2015/164,552, which is hereby incorporated by reference in its entirety.

Figure 1B:
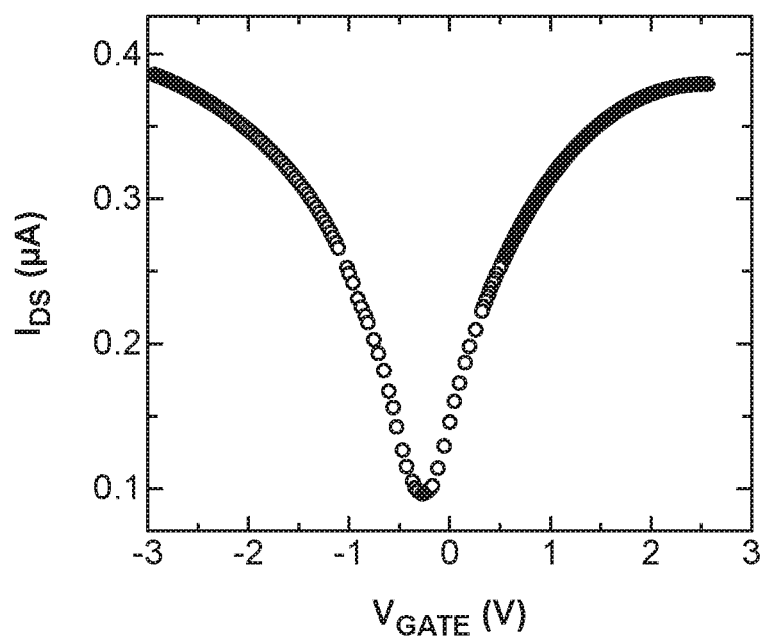
FIG. 1B depicts an embodiment of the prior art, showing current between source and drain as controlled by gate voltage.

FIG. 1B illustrates electric current between the source and drain as controlled by gate voltage. By varying on the direction and magnitude of the gate voltage, the resulting curve of current flow the source and drain takes a "V" shape. At the tip of the V-shaped curve, small changes in gate voltage result in significant and detectable changes in channel current ($I_{DS}$), and tends to plateau out at the two ends of the V-shaped curve.

Gateless Field Effect Transistors

In one aspect, disclosed herein is a new type of field effect transistors (FETs) that do not have a physical gate.

Figure 2A:
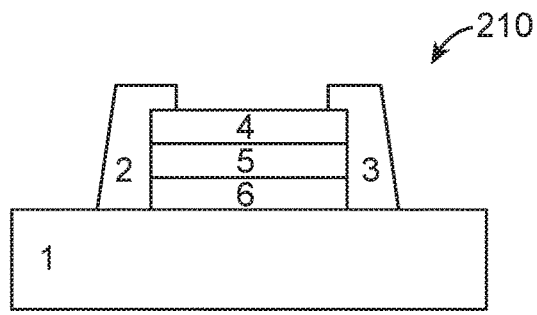
FIG. 2A depicts an exemplary embodiment, showing a gateless graphene field-effect (g-gFET).
Figure 2B:
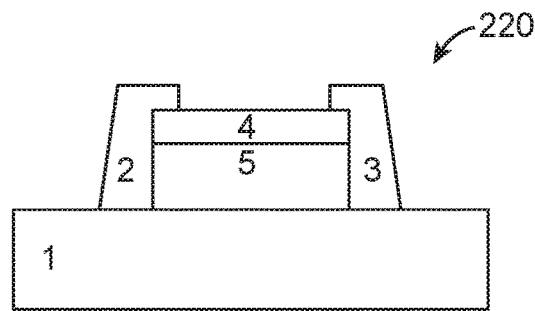
FIG. 2B depicts an exemplary embodiment, showing a g-gFET.
Figure 2C:
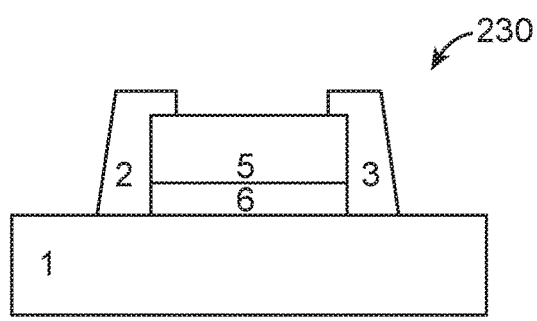
FIG. 2C depicts an exemplary embodiment, showing a g-gFET.
Figure 2D:
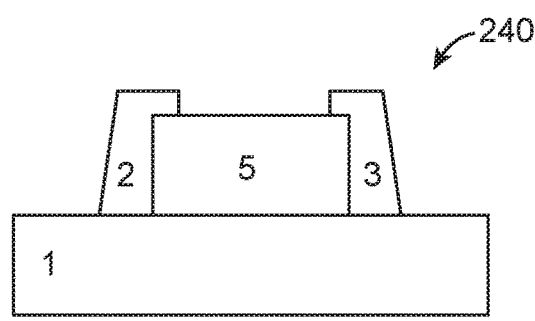
FIG. 2D depicts an exemplary embodiment, showing a g-gFET.

FIGS. 2A through 2D depicts various embodiments of FETs that do not have a physical gate. FIG. 2A depicts an example graphene-based FET 210, which includes a substrate 1, a source electrode 2, a drain electrode 3, receptors 4, a graphene layer 5, and back polymer 6. As disclosed herein, substrate 1 can be polyamide, PET, PDMS, PMMA, other plastics, silicon dioxide, silicon, glass, aluminum oxide, sapphire, germanium, gallium arsenide, indium phosphide, an alloy of silicon and germanium, fabrics, textiles, silk, paper, cellulose based materials, insulator, metal, semiconductor, can be rigid, flexible or any combination thereof. In some embodiments, substrate 1 can be a silicon carbide substrate and graphene layer 5 can be epitaxially grown on the silicon carbide substrate directly by sublimation of silicon from the silicon carbide substrate (FIG. 2B).

Source electrode 2 is the electrode region in a field-effect transistor from which majority carriers flow into the inter-electrode conductivity channel. Exemplary material that can be used as a source electrode includes but is not limited to silver, gold, carbon, graphite ink, conductive fabrics, conductive textiles, metals, conductive materials, conductive polymers, conductive gels, ionic gels, conductive inks, non-metallic conductive materials.

Drain electrode 3 is the electrode on the opposite side from source electrode 2. Exemplary material that can be used as a source electrode includes but is not limited to silver, gold, carbon, graphite ink, conductive fabrics, conductive textiles, metals, conductive materials, conductive polymers, conductive gels, ionic gels, conductive inks, non-metallic conductive materials.

In some embodiments, graphene layer 5 can have a uniform thickness, preferably a predetermined thickness of one or more monolayers of graphene. As the thickness effects electrical properties, e.g., band gap, carrier concentration etc., a uniform and preferably predetermined thickness provides control of the sensing properties and enables the formation of reproducible devices with low variability between individual sensors.

In some embodiments, graphene layer 5 can be an epitaxial layer and the graphene layer substrate may be the substrate on which the graphene layer was epitaxially grown. By letting the graphene layer remain on the substrate of growth, it is not necessary to handle typically nano-thin graphene layers and structures. Also the risk of damaging the thin graphene layer during manufacturing of the transistor is reduced when the graphene layer can remain on the substrate.

In some embodiments, graphene layer 5 can be surface treated with receptors 4 for selectivity so that only selected types of analytes are detected by the graphene layer. Exemplary receptors 4 include but are not limited to pyrene boronic acid (PBA), N-hydroxysuccinimide ester (Pyrene-NHS), organic chemicals, aromatic molecules, cyclic molecules, enzymes, proteins, antibodies, viruses, single stranded DNAs (ssDNAs), aptamers, inorganic materials, synthetic molecules, biological molecules.

In some embodiments, graphene layer 5 and/or so that certain types of chemicals are prevented from reaching the chemically sensitive channel. The surface treatment may comprise deposition of metal particles and/or polymers.

Back polymer 6 is used to provide mechanical support to the graphene. And when doped, can add a new modality to the sensing response. For example, the back polymer can be doped with biomolecules that could also bind to specific targets and contribute to the resistance change of the transistor channel.

Devices 220, 230 and 240 are variations of device 210. In device 220, back polymer layer 6 is omitted. In device 230, receptor layer 4 is omitted. In device 240, both back polymer layer 6 and receptor layer 4 are omitted.

As disclosed herein, a device or a base device can be any of devices 210, 220, 230, and 240.

Polar Fluid Gate Terminal (PFGT)

Graphene is an allotrope of carbon in the form of a two-dimensional, atomic-scale, hexagonal lattice in which one atom forms each vertex. It is the basic structural element of other allotropes, including graphite, charcoal, carbon nanotubes and fullerenes. It can be considered as an indefinitely large aromatic molecule, the ultimate case of the family of flat polycyclic aromatic hydrocarbons. In some embodiments, graphene is a monolayer of carbon atoms. Each carbon atom in graphene has four electrons. Through three of these electrons the carbon atom binds to three nearest neighboring carbon atoms to form a hexagonal lattice. For each atom, a forth electron is delocalized on the whole graphene layer, which allows the conduction of an electron current.

When a polar fluid is deposited on a graphene layer, the special electronic characteristics of graphene will cause re-organization of the charges in the polar fluid and form a liquid induced gate voltage, which can modulate the current between the source and drain electrodes.

Figure 3A:
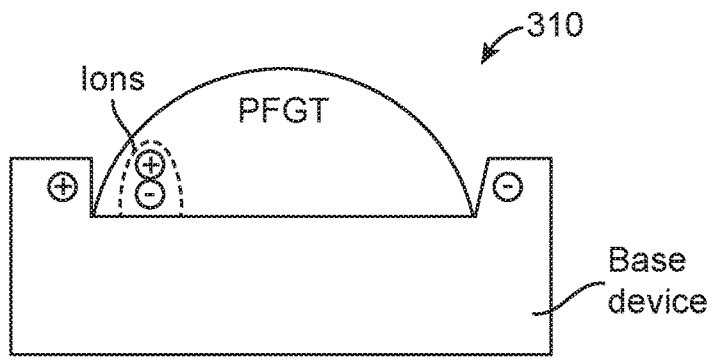
FIG. 3A depicts an exemplary embodiment, showing a polar fluid gate terminal (PFGT) where polar fluid has no motion.

FIG. 3A depicts an exemplary embodiment, showing a polar fluid gate terminal, where the polar fluid has no motion. As depicted, charges of the polar or ionic components are redistribution in the polar fluid to create a polar fluid gate terminal (PFGT) and an induced fluid gate voltage ($V_{FG}$). This voltage can result in a shift in the x-axis (voltage) in the V-shaped current vs. fluid gate voltage curve. As noted, at the tip of the V-shaped curve, small changes in gate voltage can result in significant and detectable changes in channel current ($I_{DS}$), and tends to plateau out at the two ends of the V-shaped curve. A shift towards the tip of the V-shaped curve can lead to enhanced sensitivity: very small changes in voltage in response to change in current can be detected. Similarly, very small changes in current in response to change in voltage can also be detected.

As described above, a shift towards the tip of the V-shaped curve can lead better sensitivity. Such a shift can be caused by a polar liquid induced gate voltage. In some embodiments, the polar liquid induced gate voltage is associated with the concentration of charged particles within the polar fluid. In some embodiments, the concentration can reflect the total quantity of all negatively charged particles or all positively charged particles. The shift in the V-shaped curve can correlate with a wide range of charged particle concentrations. In some embodiments, a shift is correlated with a charged particle concentration as low as 1 femto g/L (e.g., NaCl). In some embodiments, a shift is correlated with a charged particle concentration as high as 300 g/L (e.g., NaCl). The results suggest that the current sensing system is resilient and can tolerate a wide range of charge concentrations.

Figure 3B:
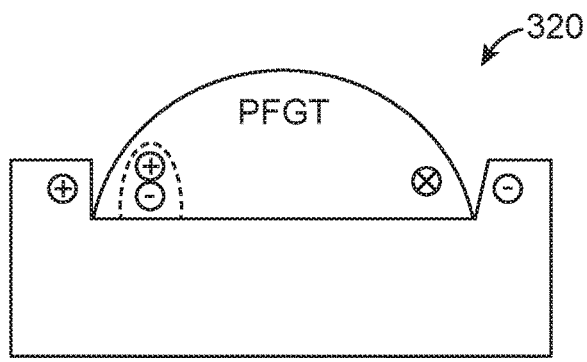
FIG. 3B depicts an exemplary embodiment, showing a polar fluid gate terminal where polar fluid flows in a first direction.

FIG. 3B depicts an exemplary embodiment, showing a polar fluid gate terminal, where the polar fluid flows in a first direction. The magnitude of the gate potential ($V_{FG}$) will be directly proportional to the flow rate of the polar fluid. The sign or direction of $V_{FG}$ will depend on the direction of flow of the polar fluid; e.g., along the source drain terminal and across the source drain terminal. For example, if the gate voltage is positive along the source drain direction, it will be negative in the reverse direction, and vice versa. When the polar fluid is flowing across the source drain voltage, if the gate voltage is positive along the Y direction, it will be negative in the −Y direction and vice versa. When the direction of the polar fluid flow changes, the direction of the gate voltage would also change.

Figure 3C:
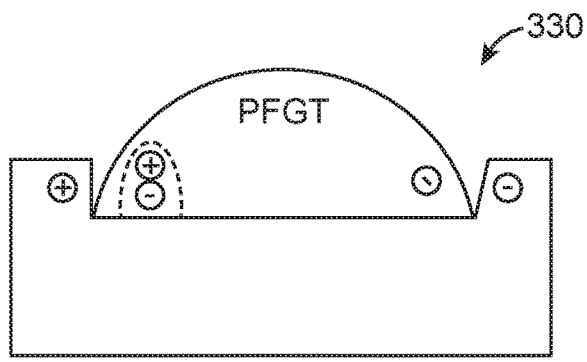
FIG. 3C depicts an exemplary embodiment, showing a polar fluid gate terminal where polar fluid flows in a second direction.

FIG. 3C depicts an exemplary embodiment, showing a polar fluid gate terminal, where the polar fluid flows in a second direction opposite to the first direction.

Detecting Gate Voltage at Polar Fluid Gate Terminal

Figure 4A:
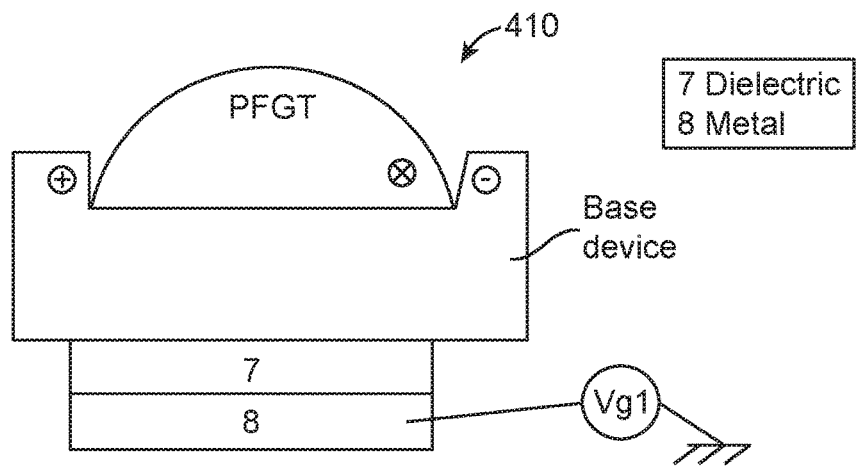
FIG. 4A depicts an exemplary embodiment, showing a base device as depicted in FIGS. 2A-2D with dielectric and gate metal. Gate potential is measured between the gate metal and the ground.
Figure 4B:
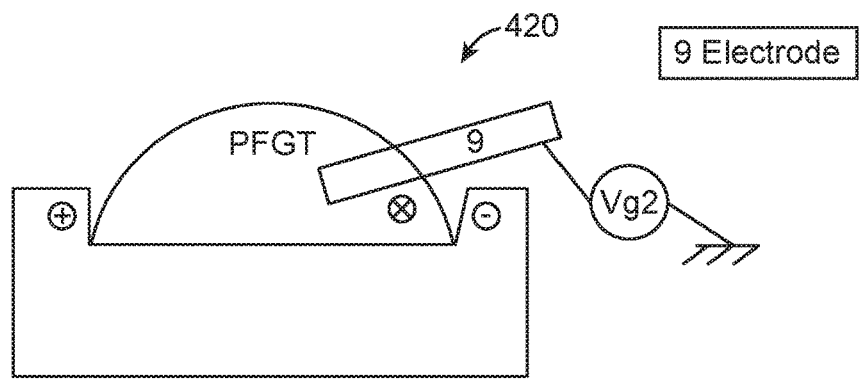
FIG. 4B depicts an exemplary embodiment, showing a base device as depicted in FIGS. 2A-2D with an added metal electrode in the PFGT. Gate potential is measured between the metal electrode and the ground.
Figure 4C:
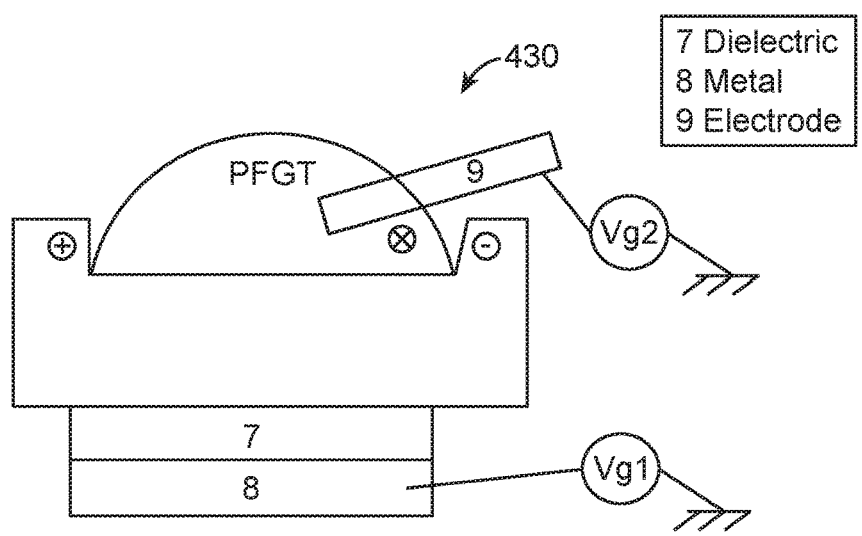
FIG. 4C depicts an exemplary embodiment, showing a base device as depicted in FIGS. 2A-2D augmented with the dielectric and gate metal, and a metal electrode in the PFGT. Two gate potentials are measured as indicated.

FIGS. 4A through 4C illustrate set up by which gate voltage at a polar fluid gate terminal (PFGT) is determined.

FIG. 4A depicts an exemplary embodiment, showing a base device with a dielectric layer 7 and a gate metal 8. Here the base device can be any of the devices depicted in FIGS. 2A-2D such as 210, 220, 230 and 240. Gate potential is measured between the gate metal and the ground. Dielectric layer 7 is added underneath the substrate of the base device (e.g., substrate 1 as depicted in FIGS. 2A through 2D). Gate metal 8 is added underneath dielectric layer 7. Gate metal 8 is added only to measure the induced gate voltage, no voltage will be applied through gate metal 8. In some embodiments, Vg1 can vary in non-linear way depending on the PFGT device characteristics and type of channel. For example, if the channel is graphene (ambipolar), Vg1 can follow the transconductance response typical to a graphene device.

FIG. 4B depicts an exemplary embodiment, showing a base device as depicted in FIGS. 2A-2D with an added metal electrode in the PFGT. Gate potential is measured between the metal electrode and the ground. Vg2 is the top gate voltage formed by the double layer capacitance between added metal electrode and active channel. Vg2 can vary in non-linear way depending on the PFGT device characteristics and type of channel. For example if the channel is graphene (ambipolar), then Vg2 will follow the transconductance response typical to a graphene device (see, e.g., FIG. 23).

FIG. 4C depicts an exemplary embodiment, showing a base device as depicted in FIGS. 2A-2D augmented with the dielectric and gate metal, and a metal electrode in the PFGT. Two gate potentials are measured as indicated. The two gate potentials (Vg1 and Vg2) are electrical outputs that are modulated using the source drain current/voltage and the induced PFG. The simultaneous measurements of Vg1 and Vg2 creates a tri-gated structure that can used develop next generation microprocessors, logic gates, computational circuits, radio frequency (RF) devices, sensors, and etc.

FIG. 4C depicts an exemplary embodiment, showing a base device as depicted in FIGS. 2A-2D augmented with the dielectric and gate metal, and a metal electrode in the PFGT. Two gate voltages (e.g., Vg1 and Vg2) are supplied to the PFGT to modulate the overall electrical characteristics of the PFGT device for a desired application. The simultaneous modulation by Vg1 and Vg2 creates a tri-gated structure that can used to shift the device operation to a desired electrical performance in a more controlled fashion using minimal energy. Such a device can be utilized to develop next generation microprocessors, logic gates, computational circuits, radio frequency (RF) devices, sensors, and etc.

Figure 5A:
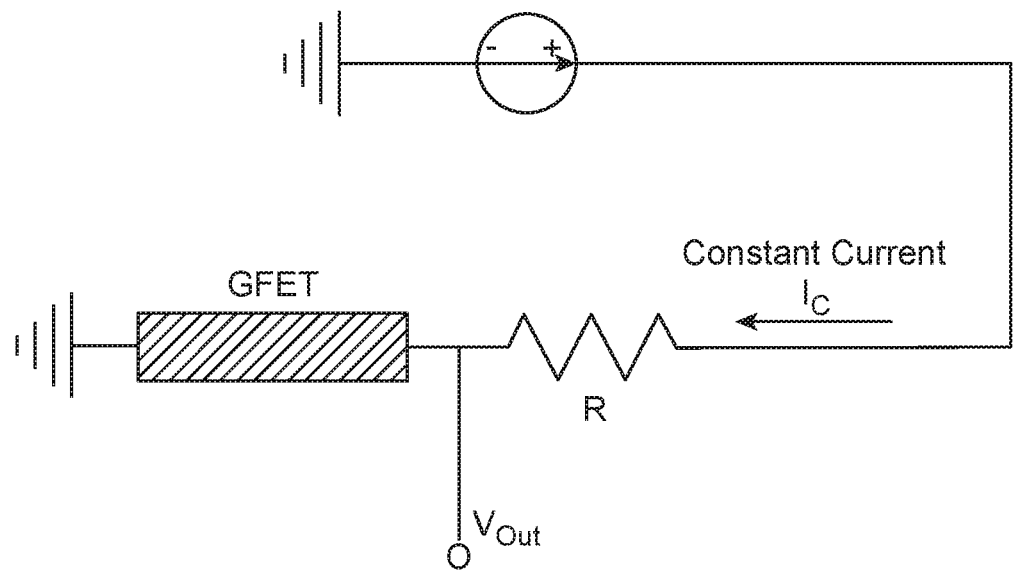
FIG. 5A depicts an exemplary embodiment, showing a GFET used in conjunction with a constant current source.

FIG. 5A depicts an exemplary embodiment, showing a circuit used for sensor readout via a polar fluid graphene field effect transistor (PFGFET). In FIG. 5A, a constant current (Ic) is supplied to the PFGFET. Output voltages (VouT) are read from across the PFGFET using a divider and current limiting resistor (R). The electrical voltage output is then calibrated to the concentrations of the analyte being sensed.

Figure 5B:
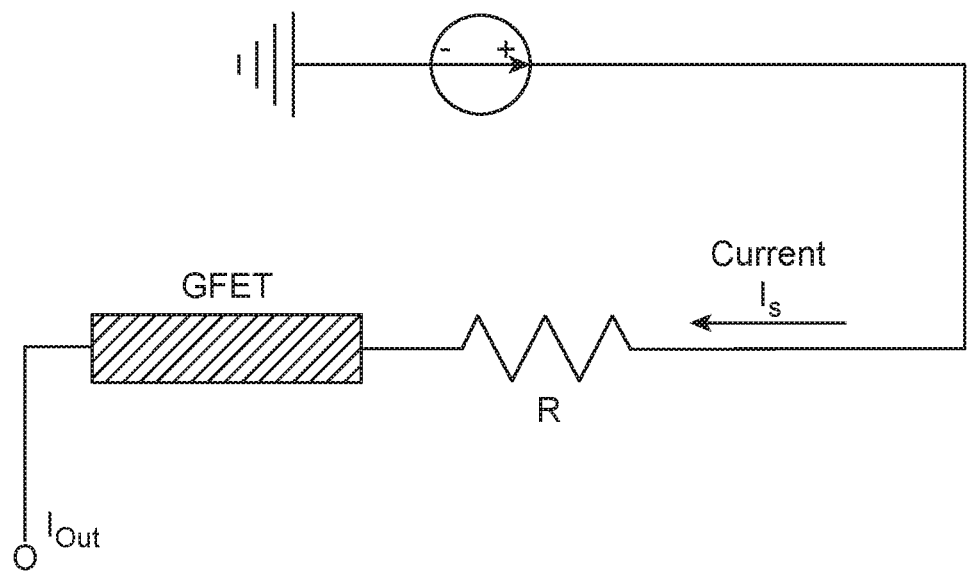
FIG. 5B depicts an exemplary embodiment, showing a GFET used in conjunction with a constant voltage source.

FIG. 5B depicts an exemplary embodiment, showing another circuit used for sensor readout via PFGFET. Here, a constant voltage (Vs) is supplied to the PFGFET. Currents or chargers (Ian) are read from the PFGFET using a current limiting resistor (R). The electrical current output is then calibrated to the concentrations of the analyte being sensed.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Experimental Conditions of Nanoscale Field Effect Transistors

Devices were fabricated with graphene as the carrier channel of a two terminal NFET without a physical gate terminal.

A polymer was disposed on graphene with thickness normally less than 0.5 mm, which was then separated from the catalytic substrate where the graphene was grown. A flexible polymer platform for the sensing system was used for staging the graphene polymer composite and two metal electrical contacts. The graphene polymer composite was bound to the flexible polymer platform. A solution of desired linker molecule is deposited on the graphene polymer composite to incubate. The excess linker molecule solution was removed from the graphene polymer composite; and the two metal electrical contacts were deposited on both edges of the graphene polymer composite.

The graphene polymer complex was then placed on a polymer substrate, such as teflon, polyimide, and etc., and then heated for 1-10 mins at 80-150 degree Celsius to remove any impurities.

The GFET sensor was then ready for use. In some cases, receptors for specific analytes were deposited on the graphene layer.

A sensor system for analyte sensing through sweat, where the sensor comprised of:
  a flexible polymer platform made of (kapton);
  a graphene polymer composite bound to the flexible polymer platform;
  a source electrode and a drain electrode located in a sensor configuration on opposing edges of the layer of graphene polymer composite also bound to the flexible polymer platform;
  each of the source and drain electrodes comprised of conductive metals;
  graphene polymer composite layer was functionalized with a linker molecule for the desired analyte biosensing, between the two electrodes; and
  the sensor system was kept in close proximity to a source of pristine sweat to be analyzed.

A method of determining analyte concentration through sweat comprised the following steps:
  applying a constant bias voltage to a functionalized graphene polymer composite sensor having a Conduction channel;
  measuring a first source-drain voltage across the sensor;
  exposing the conduction channel to the pristine sweat by bringing it in close proximity to source of sweat;
  the analyte binds to the linker molecule by releasing an electron through the linker into the channel resulting in change in potential across the channel;
  measuring a second source-drain voltage across the sensor;
  determining the concentration of analytes based upon the fractional change between the first source-drain voltage and the second source-drain voltage.

During the analysis, a fixed current or voltage was passed through the sensor. The electrical responses of the GFET sensor were recorded for analyte in polar solution, using analyte in de-ionized (DI) water as negative control. DI water responses on functionalized GFETs were also measured. Analytes included NaCl, D-glucose, and lactic acid.

Example 2

Analyses of NaCl Samples

In these examples, a fixed current or voltage was passed through a GFET. The electrical responses of the GFET sensor were recorded for the following: NaCl concentrations in DI water, or for DI water responses on functionalized GFETs.

Selectivity:

Response of various NaCl concentrations in DI water were measured on the GFET to study the sensitivity of the sensor towards NaCl. Solutions with varying concentrations of NaCl, ranging for 0 to 1 g/L in DI water were prepared. The test started with introducing 2 ul of the lowest concentrations on the GFET followed by the next higher concentration after 3 minutes and so on; for example, going from 0.05 g/L to 0.1 g/L in the example illustrated in FIG. 6. This was continued until all the concentrations were introduced onto the GFET.

Figure 6:
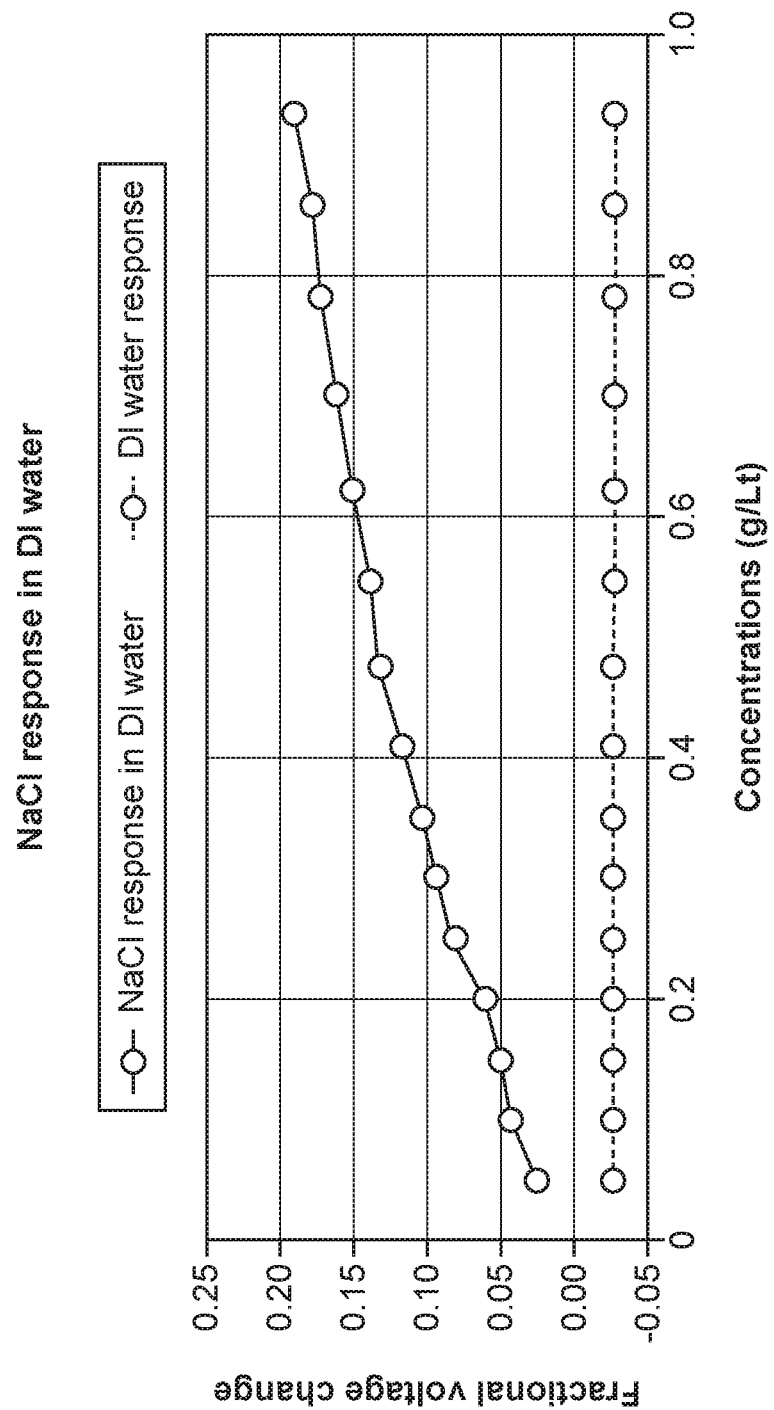
FIG. 6 illustrate an exemplary embodiment, showing selectivity measurements of NaCl response in DI water.

FIG. 6 shows that the GFET gave no significant response to just DI water and a linear response to increasing NaCl concentrations in DI water. The increasing concentrations changed the voltage across the channel, thereby showing high selectivity towards NaCl in DI water as control.

Sensitivity:

Response of various NaCl concentrations in DI water were also measured on the GFET to study the sensitivity range of the sensor towards NaCl. Solutions with exponentially increasing concentrations of NaCl, ranging from 0.1 ng/dl to 10 mg/dL in DI water, were prepared. The test started with introducing 2 ul of the lowest concentrations on the GFET followed by the next higher concentration after 3 minutes and so on. Here, concentrations increased logarithmically, for example, going from 0.1 ng/dl to 1 ng/dl, then 10 ng/dl, then 0.1 ug/dl, and so on. This was continued until all the concentrations were introduced onto the GFET.

Figure 7:
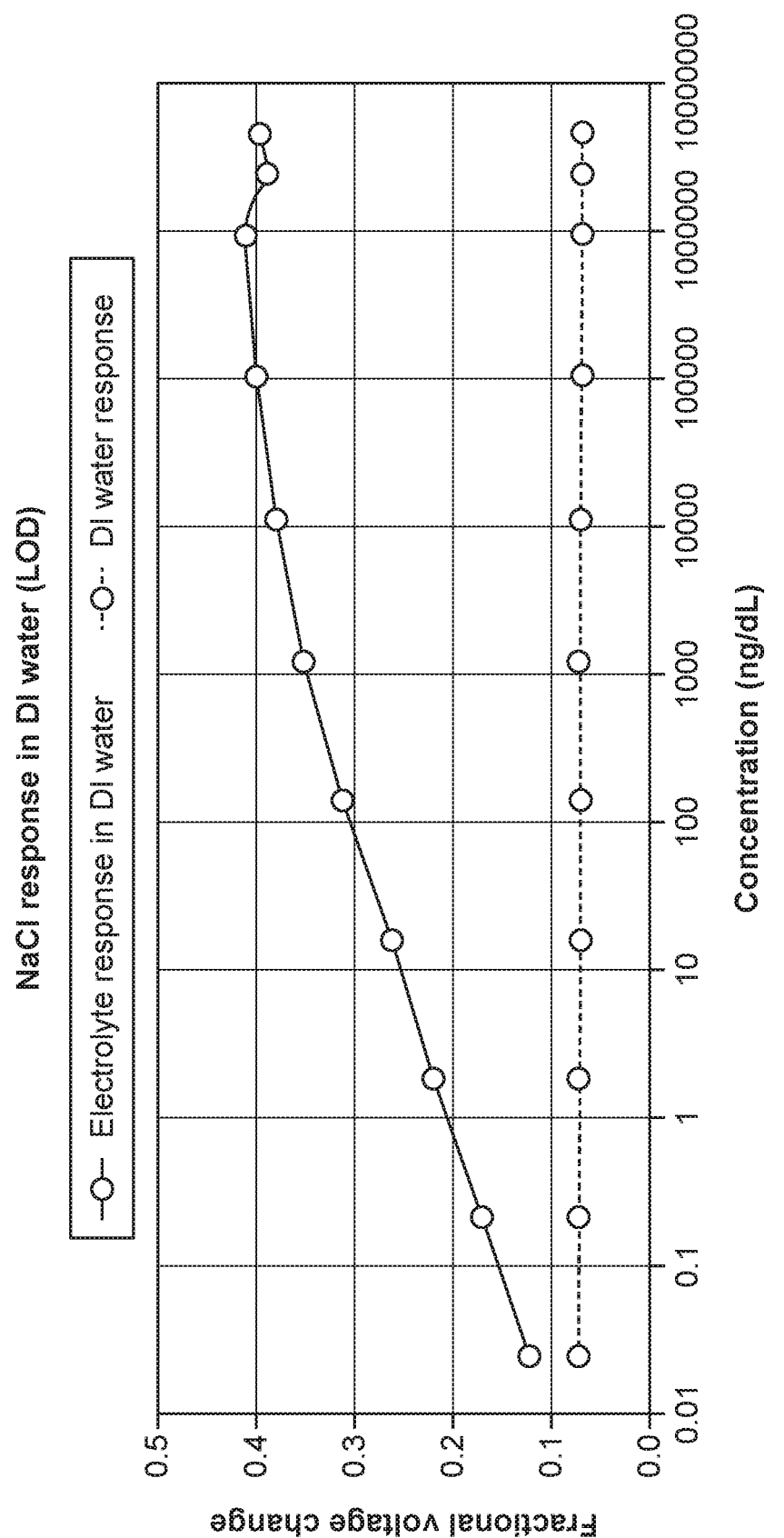
FIG. 7 illustrates an exemplary embodiment, showing sensitivity measurements for NaCl response in DI water.

FIG. 7 shows that the GFET gave no significant response to just DI water and an exponential response starting from the lowest to the highest concentration of NaCl in DI water. The increasing concentrations changed the voltage across the channel, thereby showing high sensitivity around 250 femto gram/litre towards NaCl in DI water as control.

Chloride Response in Sweat:

Measurement of chloride concentrations in human sweat was done with human subjects. The test required the subject to perform physical activity, such as running, and taking water for hydrating from time to time.

The GFETs were worn on the fore arm and lower back (eccrine sweat glands) by human subjects. Electrical responses due to the chloride concentrations in sweat were transmitted and recorded continuously (every 500 milliseconds) while the subjects were performing intense physical activity (like running). The change in Chloride concentration in sweat was observed represented by the fractional change in the voltage, as illustrated in FIG. 8.

Figure 8:
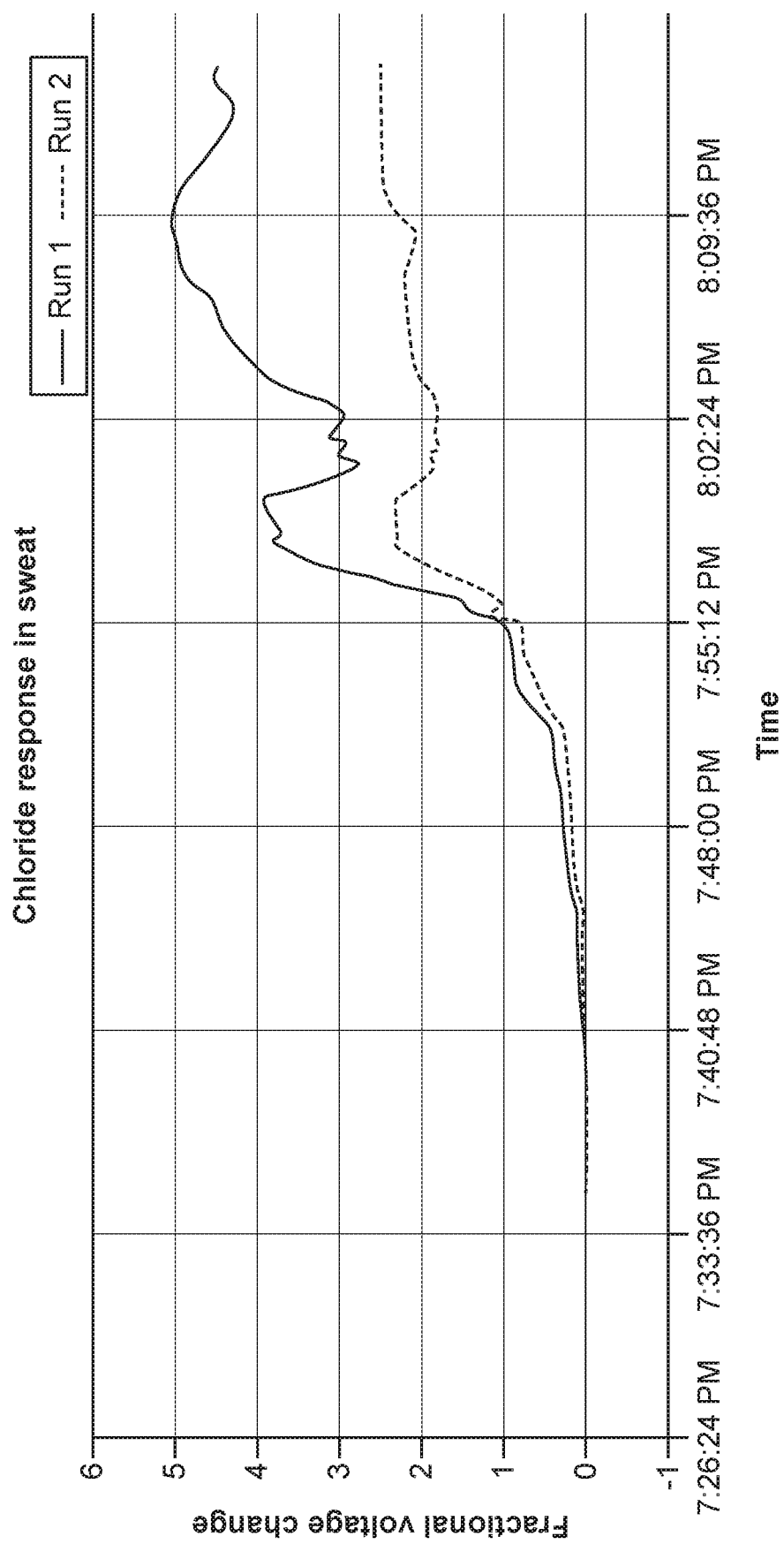
FIG. 8 illustrates an exemplary embodiment, showing chloride response in sweat.

FIG. 8 shows the real-time concentrations of sweat osmolality of two human subjects using a PFGFET attached to the skin. The osmolality concentrations in sweat directly correlated to the physical performance of the individuals. Subject 1 was a sprinter and subject 2 was a jogger. The sprinter (subject 1) ran the same distance in a quicker pace (run 1) as compared to the jogger (subject 2 and run 2). It was observed that more intense a subject's physical activity, higher the measured body osmolality concentrations. Peaks in body osmolality were observed during periods of most intense physical activity. It was also observed that the body osmolality reduced during periods of the intense physical activity. This was caused when the subject consumed too much water without adequate supplementation of salts. In the data, when the slope of the curve tends to 0, it indicates hyponatremia During this period the body tries to retain as much salt it can (to maintain the ionic balance) and thus the concentration of overall body osmolality change very slowly.

The following novel results and/or features were observed.

High Selectivity:

The GFETs (NFETs) modulated by PFGT gave a highly selective response (>97%) to NaCl concentrations in different control fluids.

High Sensitivity:

The GFETs functionalized with PBA exhibited a high sensitivity for NaCl with a limit of detection (LOD) of 250 femto gram/litre. The GFET sensors have a high signal to noise ratio, are highly selective and due to the high surface area for bonding there is higher bonding between the surface and the molecules. All these factors play a huge differentiating role, making GFETs highly sensitive.

Gate modulation due to polar molecules: In polar fluids (like water, salt etc.) it was observed that the polar molecules (like ions etc.) formed a polar fluid gate terminal (PFGT) on the NFETs. The polar molecules near the graphene surface induced a dielectric effect creating a channel for charge transfer. The gating strength of the PFGT was dependent both on the charge and concentration of the polar molecules in the fluid. Such a third polar fluid gate terminal (PFGT) modulated the electrical responses from NaCl concentrations in a polar fluid.

Continuous Monitoring:

The concentrations of the ions were measured continuously in the fluid due to the modulation of the NFET channel current from the induced Polar Fluid Gate terminal. Once the ionic solution was removed from the surface of the NFET, the electrical response of the polar fluid gated NFET went back to bare or initial value.

Induced Motion of the of the Polar Fluid Over Surface of NFET:

It was observed that the polar fluid (like NaCl in DI water) would try to immediately repel or come off from the NFET surface, due to increased hydrophobicity between NFET surface and the polar fluid. The higher the concentration of the polar molecules (e.g., NaCl) in the fluid, more the strength of the PFGT and hence more the repelling effect. This repelling effect combined with the modulation of the electrical response due to the PFGT by the NaCl molecules on the NFET allowed for a highly sensitive, selective and continuous monitoring electrolyte system.

Real-Time Continuous Chloride Monitoring in Human Sweat:

As an example, GFETs were worn on the fore-arm and lower back (eccrine sweat glands) by human subjects. Sweat is diluted and ultra-filtered blood. Electrical responses due to the chloride concentrations in sweat were transmitted and recorded continuously (every 500 milliseconds) while the subject was performing a) intense physical activity (workouts) b) no intense physical activity (like sitting on an office desk and eating). It was observed that the background ionic concentrations in sweat (primarily NaCl) formed a PFGT over the two terminal GFET devices. The changes in gating strength of the induced PFGT on the GFET due to the Cl— ions allowed for the continuous non-invasive monitoring of the Cl ionic molecules in human sweat. It was observed that sweat is a very good polar fluid to measure chloride concentrations continuously as it is very diluted and ultra-filtered.

Example 3

Analyses of D-Glucose Samples

In these examples, fixed current or voltage was passed through the GFET.

The electrical responses of the GFET/PBA sensor were recorded for the following:
- D-Glucose concentrations in DI water
- D-Glucose concentrations in artificial sweat (DI+NaCl+ Lactic acid)
- D-glucose concentrations in DI water on non-functionalized GFETs
- Lactose concentrations (control 1) in DI water on functionalized devices
- Artificial sweat concentrations (control 2) on functionalized devices
- DI water responses on functionalized GFETs
- Human sweat glucose measurements: Real-time continuous monitoring of glucose concentrations were performed in human sweat using wearable GFET/PBA sensors. The real-time continuous sweat glucose responses were correlated with blood glucose measurements, using commercially available blood glucose meters Functionalization:

As an example, Graphene FETs were functionalized with linker molecule (lock) that specifically binds to the glucose molecule in fluids. As an example, the GFET was functionalized with Pyrene Boronic Acid (PBA). Pyrene Boronic Acid bonds to the Graphene surface using pi-pi bond. PBA forms a reversible boron-anion complex with D-glucose. Fabrications steps are the following:
- A polymer was disposed on graphene with thickness normally less than 0.5 mm, which is then separated from the catalytic substrate it was grown on.
- The graphene polymer complex was then placed on a polymer substrate, such as teflon, polyimide, etc. and heated for 1-10 mins at 80-150 degree Celsius to remove any impurities.
- The graphene polymer was then introduced to a solution of PBA for 5-20 minutes for functionalization at room temperature
- After the functionalization step the sensor is ready for use.

Response of various D-Glucose concentrations in DI water were measured on the GFET to study the sensitivity of the functionalized sensor towards D-Glucose.

Solutions with varying concentrations of D-Glucose, ranging for 0.1 to 100 mg/dL in DI water, were prepared, as well as varying concentrations of lactose in DI water were prepared. The test started with introducing 5u1 of the lowest concentrations on the GFET followed by the next highest concentration after 3 minutes and so on. This was continued until all the concentrations were introduced onto the GFET.

Figure 9:
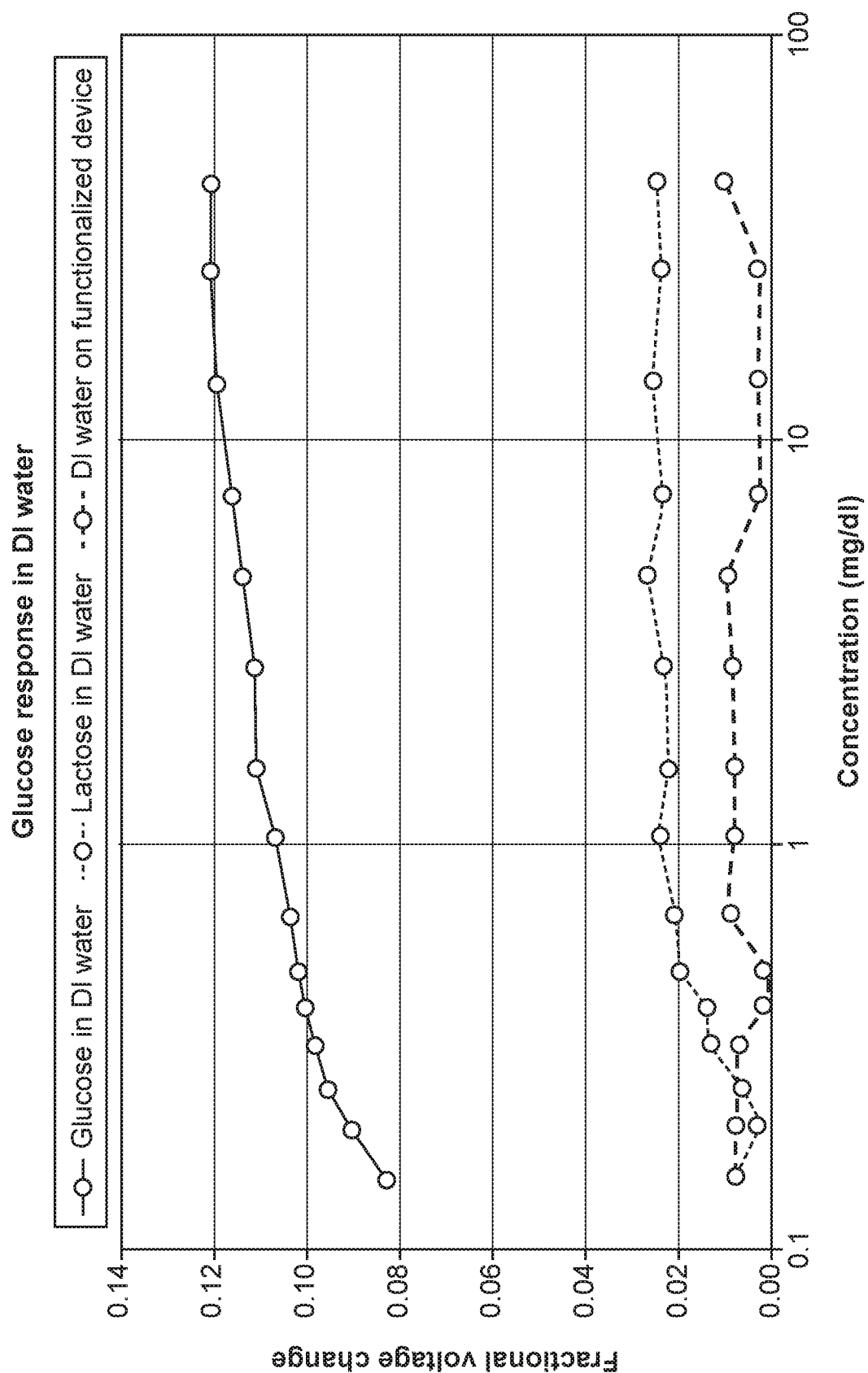
FIG. 9 illustrates an exemplary embodiment, showing selectivity measurements of Glucose response in DI water.

FIG. 9 shows that the GFET gave no significant response to just DI water or to lactose solutions and an exponential response to increasing D-Glucose concentrations in DI water. The increasing concentrations changed the voltage across the channel, thereby showing high selectivity towards D-Glucose with DI water as control.

Glucose Response in NaCl Vs Glucose Response in DI Water:

Response of various D-Glucose concentrations in DI water and NaCl solutions were measured on the GFET to study the sensitivity of the functionalized sensor towards D-Glucose in DI water vs D-Glucose in NaCl and to understand the effect of NaCl solutions.

Solutions with varying concentrations of D-Glucose, ranging from 0.1 to 100 mg/dL, in DI water and NaCl, respectively, were prepared. The test started with introducing 5 u1 of the lowest concentrations on the GFET followed by the next higher concentration after 3 minutes and so on. Here, the concentrations increased logarithmically. This was continued until all the concentrations were introduced onto the GFET.

Figure 10:
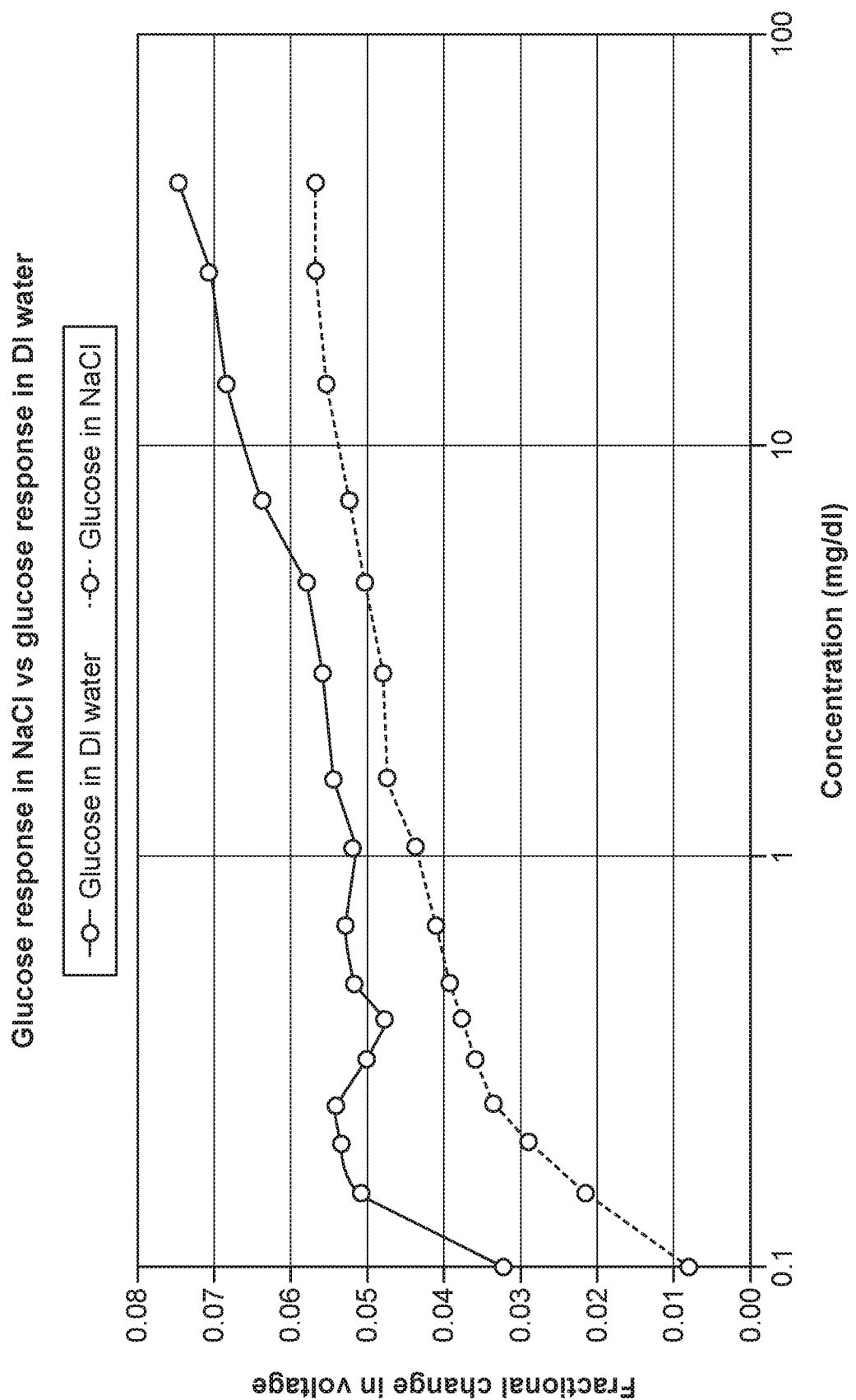
FIG. 10 illustrates an exemplary embodiment, showing glucose response in NaCl vs glucose response in DI water.

FIG. 10 shows that the D-Glucose response in NaCl is more amplified than D-Glucose response in DI water. The polar solution providing the PFGT on the GFET amplified the electrical response across the channel thereby increasing sensitivity and providing reversibility.

Selectivity Measurements of Glucose Response in NaCl Solution:

Response of various D-Glucose concentrations in NaCl were measured on the GFET to study the sensitivity of the functionalized sensor towards D-Glucose.

Solutions with varying concentrations of D-Glucose, ranging from 0.1 to 100 mg/dL, in NaCl solutions, were prepared, as well as varying concentrations of NaCl in DI water were prepared. The test started with introducing 5u1 of the lowest concentrations on the GFET followed by the next higher concentration after 3 minutes and so on. Here, the concentrations increased logarithmically. This was continued until all the concentrations were introduced onto the GFET.

Figure 11:
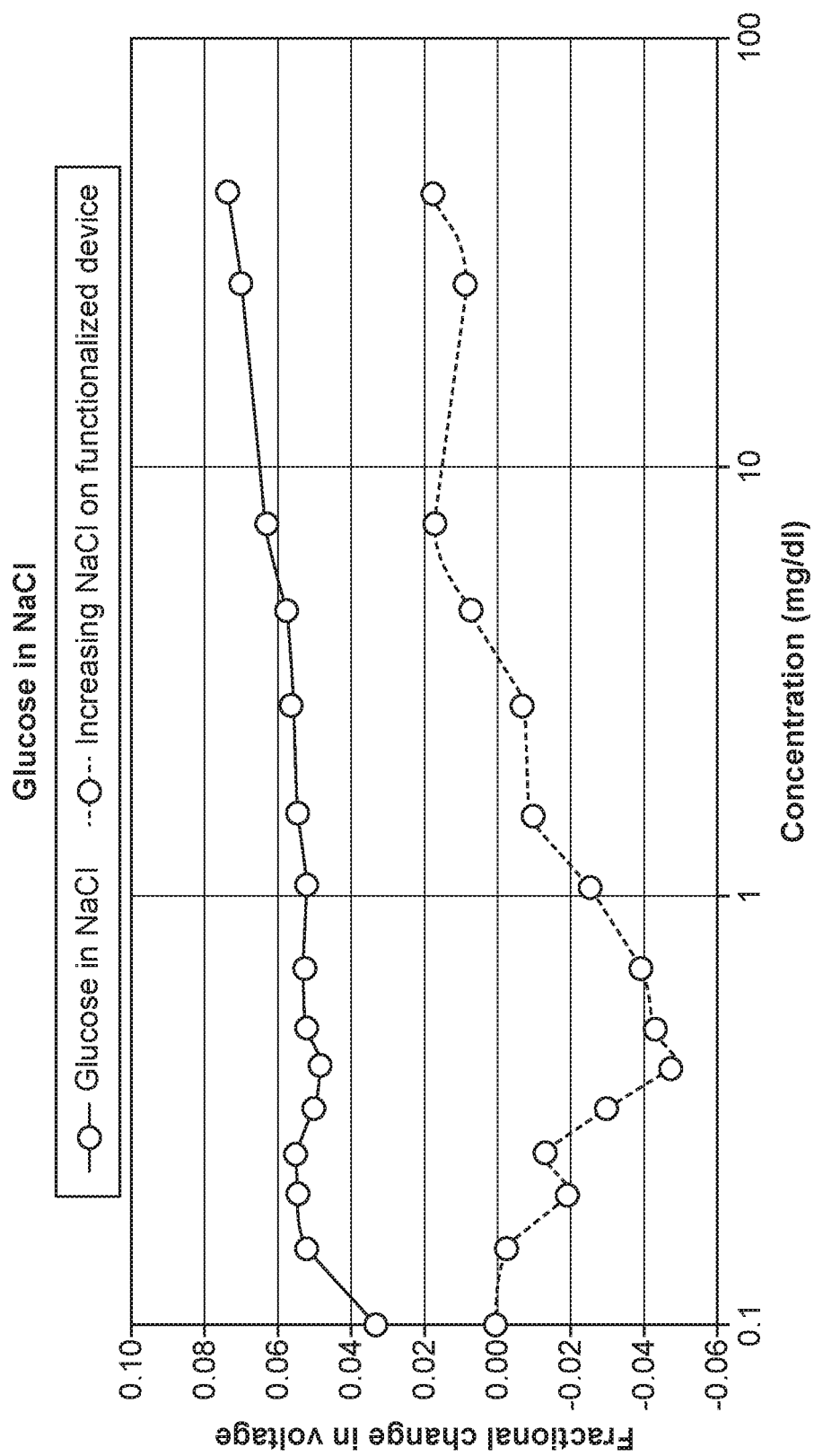
FIG. 11 illustrates an exemplary embodiment, showing selectivity measurements of Glucose response in NaCl water.

FIG. 11 shows that the GFET gave no significant response to just NaCl solutions and a linear response to solutions of increasing D-Glucose concentrations in fixed NaCl concentration versus solutions of increasing NaCl concentrations. The increasing concentrations changed the voltage across the channel, thereby showing high selectivity towards D-Glucose. The GFETs (NFETs) functionalized with PBA gave a highly selective response (>95%) to glucose concentrations.

FIG. 11 gives an idea that the functionalized glucose sensor isn't sensitive to NaCl (as the orange curve is fairly flat), whereas the glucose curve is increasing with increasing conc of glucose present in NaCl solution.

Sensitivity Measurements of D-Glucose Response in DI water: Response of various D-Glucose concentrations in DI were measured on the GFET to study the sensitivity range of the functionalized sensor towards D-Glucose.

Solutions with exponentially increasing concentrations of glucose, ranging from 250 femto gram/L to 100 mg/L in DI water, were prepared. The test started with introducing 3 rounds of $5u1$ DI water every 3 minutes followed by $5u1$ of the lowest concentrations, on the GFET followed by the next higher concentration after 3 minutes and so on. Here, the concentrations increased logarithmically; e.g., from 0.25 pg/1, then 2.5 pg/1 and so on. This was continued until all the concentrations were introduced onto the GFET.

Figure 12:
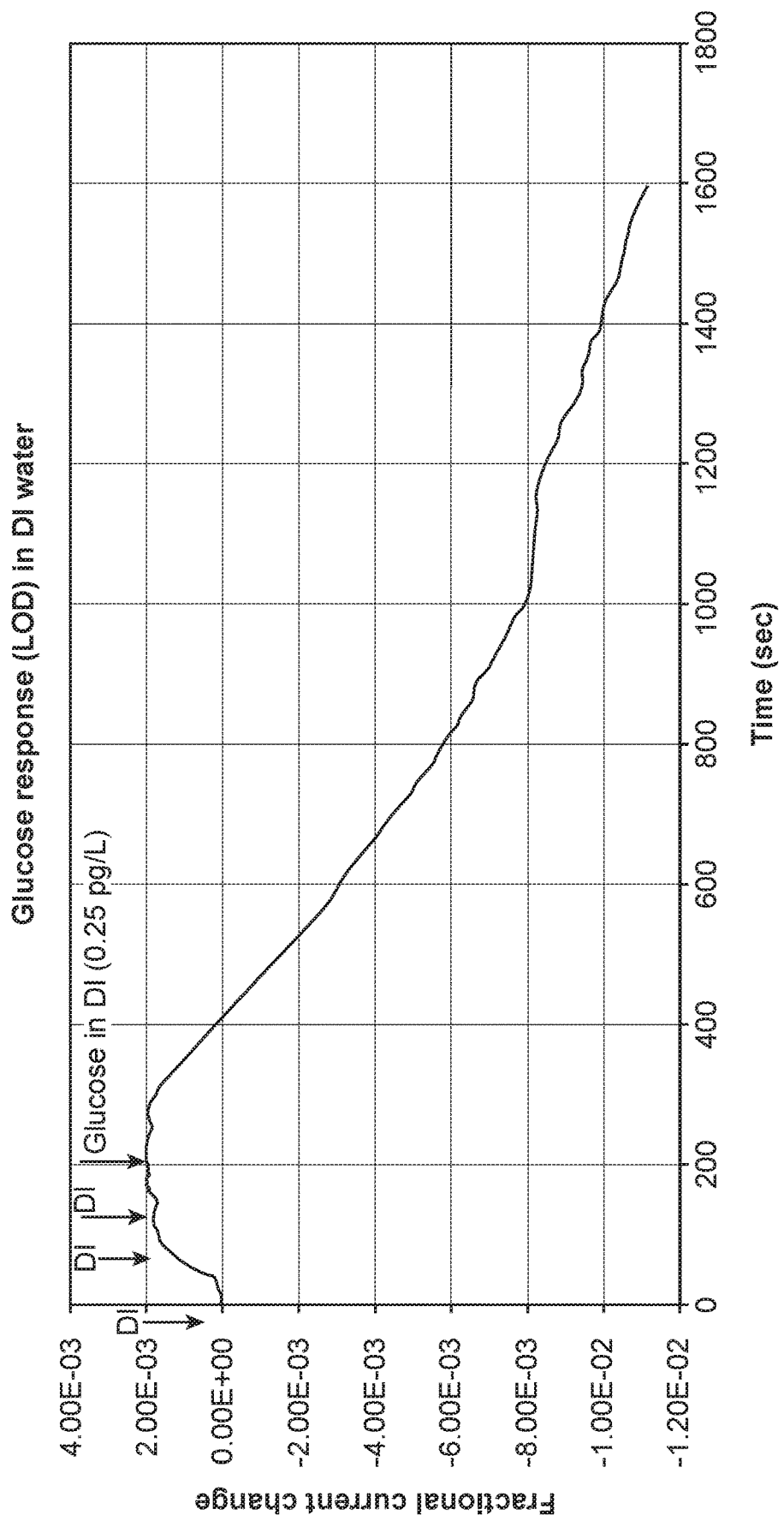
FIG. 12 illustrates an exemplary embodiment, showing sensitivity measurements of D-Glucose response in DI water.

FIG. 12 shows that the GFET gave no significant response to just DI water and a linear response starting from the lowest to the highest concentration, with increasing concentrations the current across the channel changed, thereby showing high sensitivity around 250 femto gram/litre (i.e., 1.38e−12=101/1) towards D-glucose.

Figure 13:
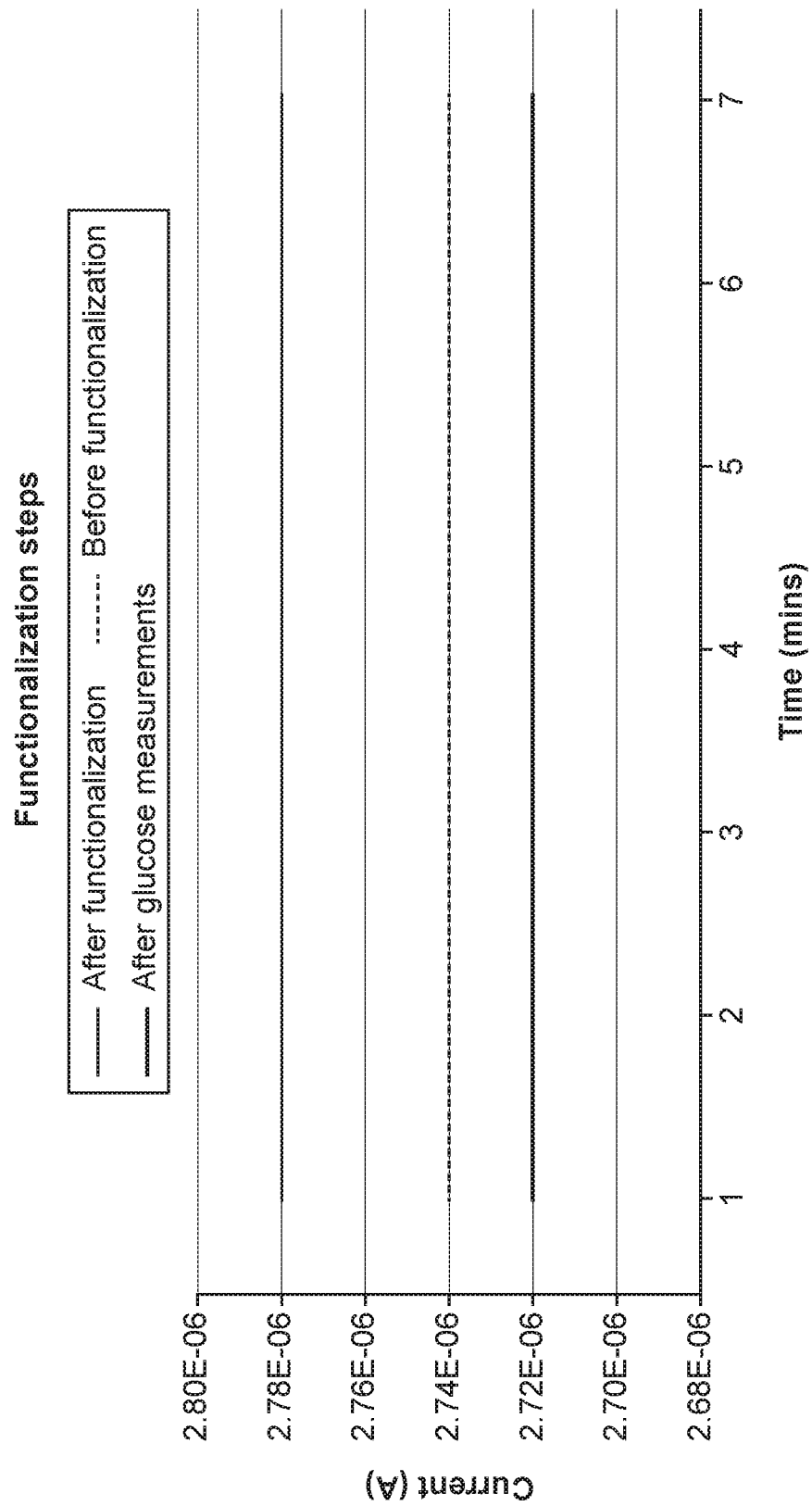
FIG. 13 illustrates an exemplary embodiment, showing functionalization steps visualized through the GFET fabrication.

Functionalization Steps:

Shown in FIG. 13 are the current response for graphene sensor, before functionalization, after functionalization and after glucose is introduced on the sensor. This helps in understanding each stage of the GFET fabrication step and how after each stage the current response of the GFET changes. For example, it was shown in FIG. 13 that the current response increases after functionalization (orange) as compared to the before functionalization (blue) this happens because linker molecules are bound by pi-pi bond and the overall charge on the surface of the graphene increases. The linker molecule attracts the glucose molecules and binds to it by using these charge clouds thereby reducing the current on the GFET as compared to its previous state.

D-Glucose Response in Sweat and Blood:

Measurement of glucose concentrations in human sweat was done with human subjects. The test required the subject to perform physical activity, such as running, and taking blood samples to measure blood glucose using a blood glucose meter every few minutes. The GFETs are worn on the fore arm and lower back (eccrine sweat glands) by human subjects. Electrical responses due to the D-Glucose concentrations in sweat were transmitted and recorded continuously (every 500 milliseconds) while the subjects were performing intense physical activity (like running).

In this particular case, the physical activity was eating food. As a subject start seating, his glucose will start going up as can be seen in both sweat and blood glucose. After the person is done eating, the glucose level will start to come down and stabilize.

In case of running, as one starts running, the body uses the glucose and break it down to get energy for running. Hence you will see a reduction in glucose. However, after some point, your body's insulin comes into play and the overall glucose value will start going up again.

Figure 14:
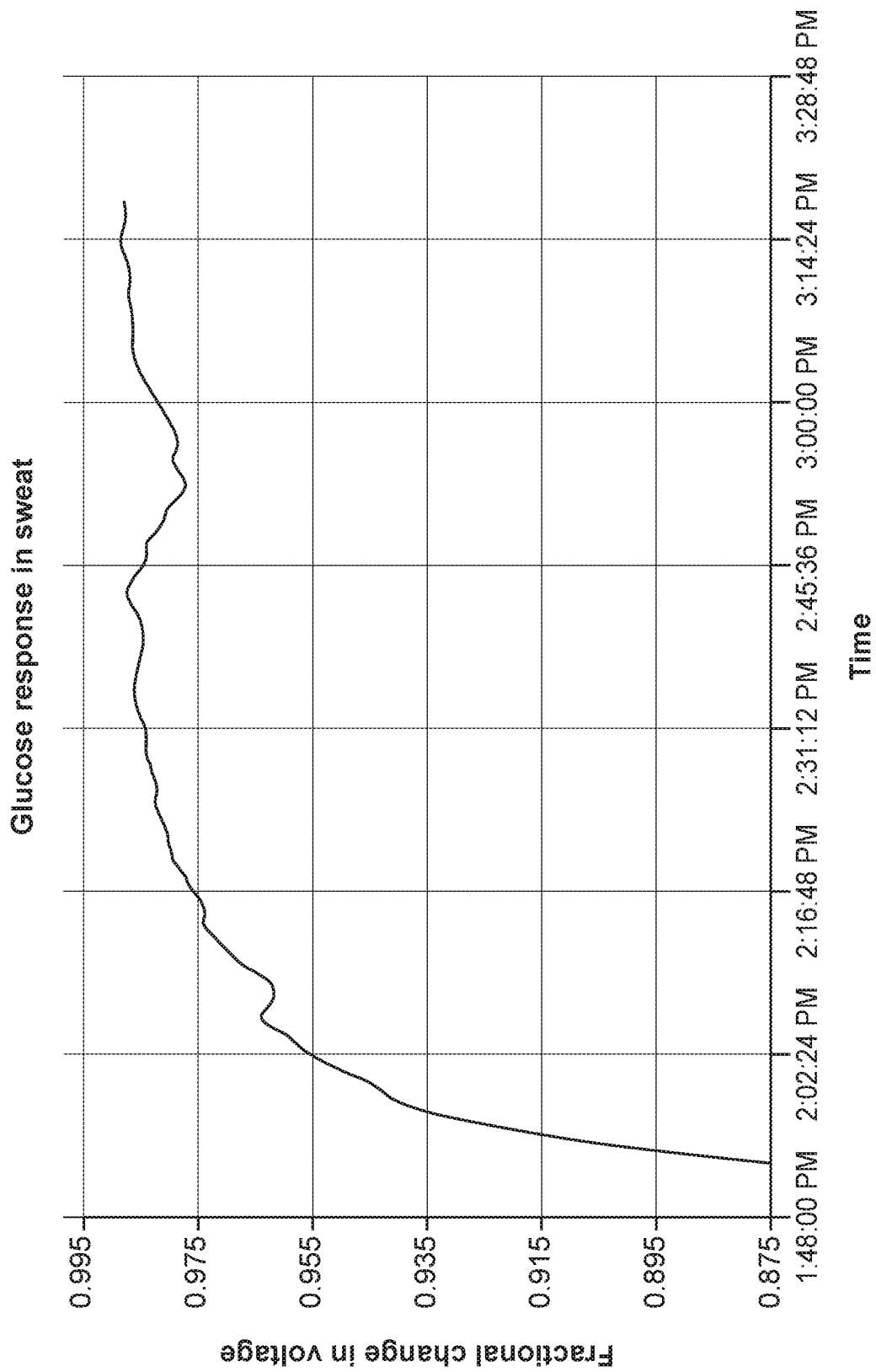
FIG. 14 illustrates an exemplary embodiment, showing D-glucose response in sweat.

FIG. 14 shows the change in D-Glucose concentration in sweat, as represented by the fractional change in the voltage.

Figure 15:
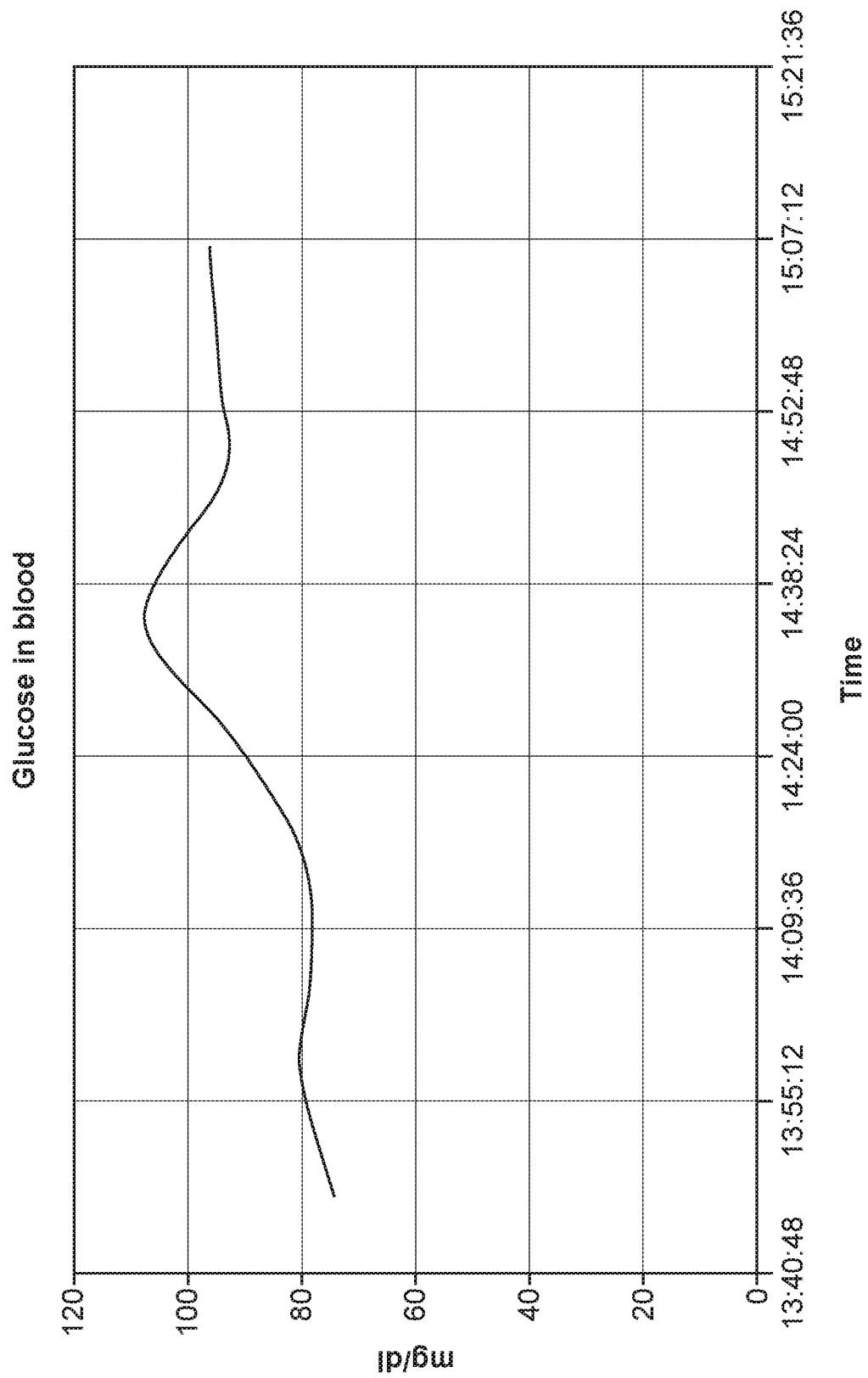
FIG. 15 illustrates an exemplary embodiment, showing D-glucose response in blood.

The blood glucose data in FIG. 15 was also plotted against time for the entire duration of the workout. The sweat glucose measurements were correlated with blood glucose measurements. Here, the sweat glucose values for the corresponding blood glucose values were plotted against blood (blood vs sweat) to get a correlation R2, which provided an idea about how well sweat glucose matched with blood glucose.

Figure 16:
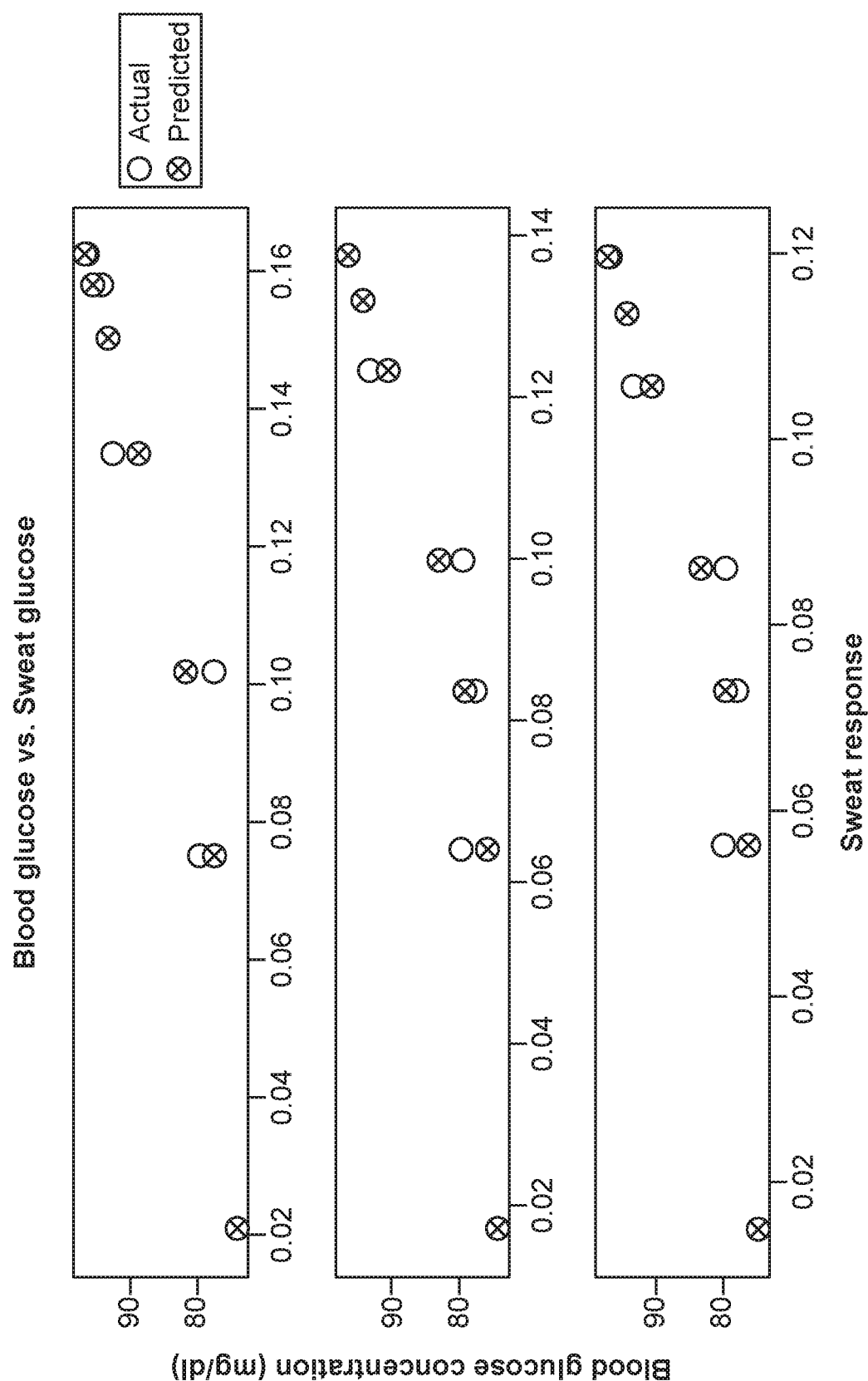
FIG. 16 illustrates an exemplary embodiment, showing measurements correlation between blood glucose and sweat glucose.

FIG. 16 further shows measurements correlation between blood glucose and sweat glucose. Here, 3 different sensors were used for the same person for the same time. Over 150 curves of sweat glucose were collected from 10 human subjects along with their blood glucose for the entire duration of the study, for correlation. The subjects performed physical activities (workouts, running, etc.) or no physical activity (sitting on a desk, etc.). For these 150 curves the calculated correlation was R2=84% between sweat and blood, also shown in FIG.

The following novel results and/or features were observed.

High Selectivity:

The GFETs (NFETs) functionalized with PBA gave a highly selective response (>95%) to glucose concentrations in different control fluids.

High Sensitivity:

The GFETs functionalized with PBA exhibited a high sensitivity for D-Glucose with a limit of detection (LOD) of 250 femto gram/litre, i.e., 1.38e-1-2 mmol/l. The existing glucose meters have an LOD between 0.3-1.1 mmol/l. The GFET functionalized with PBA is approx. 1010 times more sensitive than the existing standard glucose measurement devices. The GFET sensors have a high signal to noise ratio, are highly selective and due to the high surface area for bonding there is higher bonding between the surface and the receptor molecules. All these factors play a huge differentiating role in making GFETs highly sensitive.

Gate Modulation Due to Polar Molecules:

In polar fluids (like water, salt etc.) it was observed that the polar molecules (such as ions) formed a polar fluid gate terminal (PFGT) on the NFET. The polar molecules near the graphene surface induced a dielectric effect creating a channel for charge transfer. The gating strength of the PFGT was dependent on both the charge and concentration of the polar molecules in the fluid. Such a third polar fluid gate terminal (PFGT) modulated the electrical responses from the glucose concentrations in a polar fluid.

Continuous Glucose Monitoring:

The reversibility of the PBA-glucose bond on the graphene surface was greatly enhanced by the charge modulation due to the polar fluid gate terminal on the NFET formed in polar fluids. The higher the concentration of the polar molecules (like ions etc.) in the polar fluid, more the reversibility of the PBA-D-Glucose bond was observed. Once the glucose concentration bound on the sensor is higher than the glucose concentration in sweat, due to its Gibbs free energy, the glucose molecules get unbound from the PBA and the reversible nature is observed, this is clearly seen in the electrical responses recorded in FIG. 14 as the concentration of glucose drops momentarily. This allowed for a reusable and real-time continuous monitoring of D-Glucose molecules in polar fluids.

Reusability of the Glucose Sensor Due to Motion of the Polar Fluid Over the Sensor Surface:

It was observed that the motion of the polar fluid (like glucose in salt) over the NFET enhanced the removal of the bound glucose molecules from the linker molecule. As an example, when the glucose solutions were removed from the surface of the graphene in the GFET, the electrical response of the GFET went back to the bare value.

Induced Motion of the of the Polar Fluid Over Surface of NFET:

It was observed that the polar fluid (like glucose in salt) would try to immediately repel or come off from the NFET surface, due to increased hydrophobicity between NFET surface and the polar fluid. The higher the concentration of the polar molecules in the fluid, more the strength of the PFGT and hence more the repelling effect. This repelling effect combined with removal of the bound glucose molecules (described above in section e) and the modulation of the electrical response due to the PFGT on the NFET allowed for a highly sensitive, selective and continuous monitoring glucose system.

Real-Time Continuous Glucose Monitoring in Human Sweat:

GFETs functionalized with PBA were worn on the formarm and lower back (eccrine sweat glands) by human subjects. Sweat is diluted and ultra-filtered blood. Electrical responses due to the glucose concentrations in sweat were transmitted and recorded continuously (every 500 miliseconds) while the subject was performing: a) intense physical activity (workouts) and b) no intense physical activity (like sitting on an office desk and eating). The sweat glucose responses were correlated to blood glucose readings taken every few minutes using a blood glucose meter over the length of the activity (typically 20 minutes to over 6 hours). It was observed that the background ionic concentrations in sweat (primarily NaCl) formed a PFGT over the two terminal GFET/PBA devices. The enhanced reversibility between the PBA and D-glucose bond due to the PFGT on the GFET allowed for the continuous non-invasive monitoring of the glucose molecules in human sweat. A correlation of 84% (R2) was calculated between blood glucose and sweat glucose measurements. The correlation was calculated for over 150 sweat glucose responses collected from 10 human subjects under various physical activity conditions. It was observed that sweat is a very good polar fluid to measure glucose continuously as it is very diluted and ultra-filtered.

Example 4

Analyses of Lactic Acid Samples

In these examples, a fixed current or voltage was passed through the GFET.

Functionalization:

Graphene FETs were functionalized with linker molecule (lock) that specifically binds to the lactic acid molecules in fluids. As an example, the GFET was functionalized with Lactate Oxidase (LOx) to the Graphene surface using an intermediate pyrene-NHS linking chemistry

- A polymer is disposed on graphene with thickness normally less than 0.5 mm, which is then separated from the catalytic substrate it was grown on.
- The graphene polymer complex is then placed on a polymer substrate, such as teflon, polyimide, etc. and heated for 1-10 mins at 80-150 degree celcius to remove any impurities.
- The graphene polymer is then introduced to a solution of pyrene-NHS for 5-20 minutes for functionalization at room temperature
- The graphene polymer is then introduced to a solution of LOx for binding for 520 mins at room temperature After the functionalization step the sensor is ready for use.

The electrical responses of the GFET/LOx sensor were recorded for the following by:

- Lactic acid concentrations in DI water
- Lactic acid concentrations in artificial sweat (DI+NaCl+Glucose)
- Lactic concentrations in NaCl on non-functionalized GFETs
- Lactic acid concentrations in NaCl on functionalized GFETs
- Artificial sweat concentrations (control 2) on functionalized devices
- DI water responses on functionalized GFETs Selectivity Measurements of Lactic Acid Response in DI Water:

Response of various lactic acid concentrations in DI were measured on the GFET to study the sensitivity of the functionalized sensor towards lactic acid. Solutions with varying concentrations of lactic acid ranging for 0-25 mM in DI water were prepared. The test started with introducing 2 ul of the lowest concentrations on the GFET followed by the next highest concentration after 3 minutes and so on. This was continued until all the concentrations were introduced onto the GFET.

Figure 17:
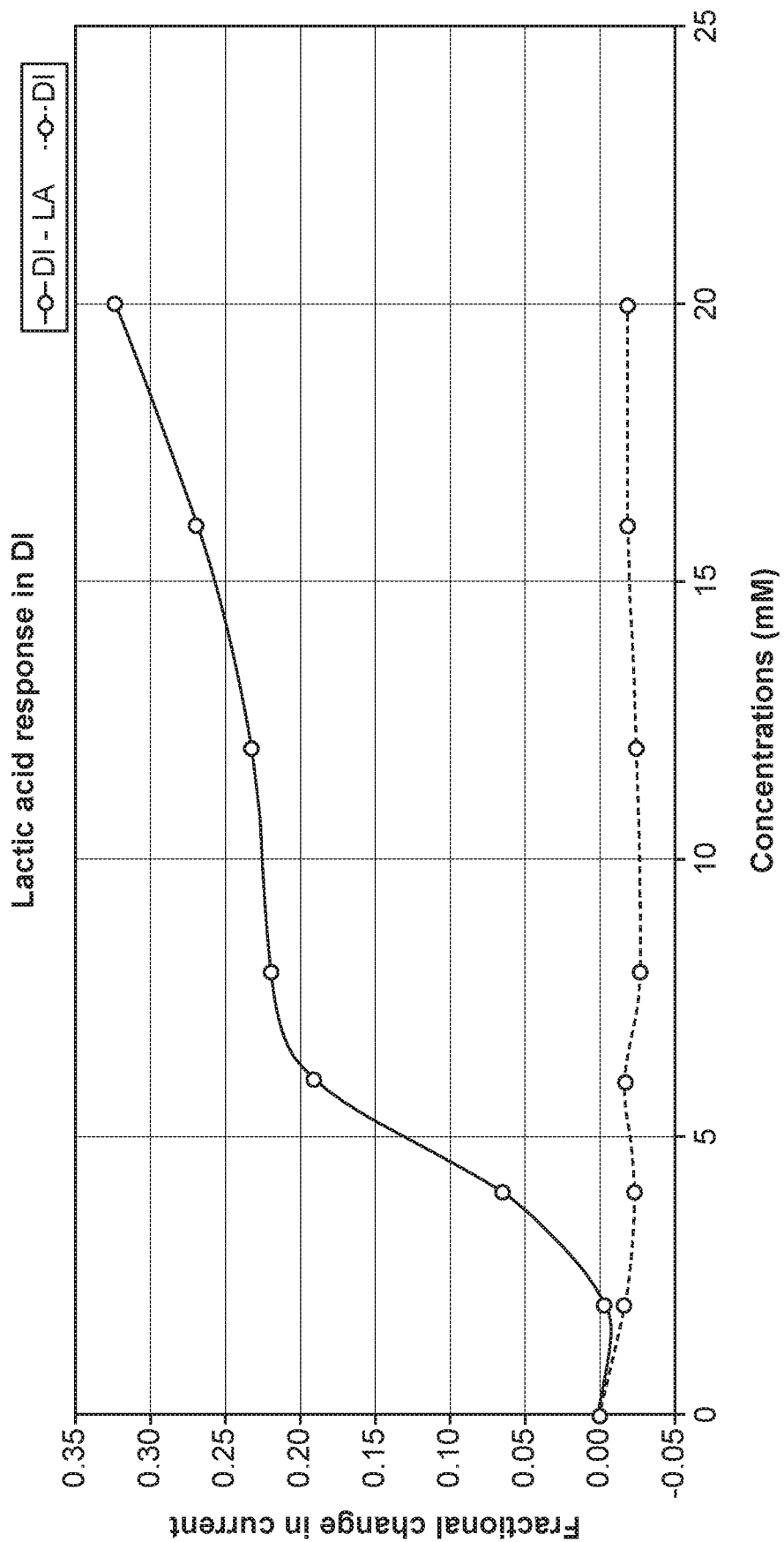
FIG. 17 illustrates an exemplary embodiment, showing selectivity measurements of lactic acid response in DI water.

FIG. 17 shows that the GFET gave no significant response to just DI water and a polynomial response to increasing lactic acid concentrations in DI water, the increasing concentrations changed the voltage across the channel, thereby showing high selectivity towards lactic acid in DI water, using DI water as the control.

Selectivity Measurements of Lactic Acid Response in Various Solutions:

Response of various lactic acid concentrations in various solutions were measured on the GFET to study the sensitivity of the functionalized sensor towards lactic acid and response on a non-functionalized sensor. Solutions with varying concentrations of lactic acid ranging for 0-25 mM in NaCl and NaCl-Glucose were prepared. The test started with introducing 2 ul of the lowest concentrations on the GFET followed by the next highest concentration after 3 minutes and so on. This was continued until all the concentrations were introduced onto the GFET, separately for each solution.

Figure 18:
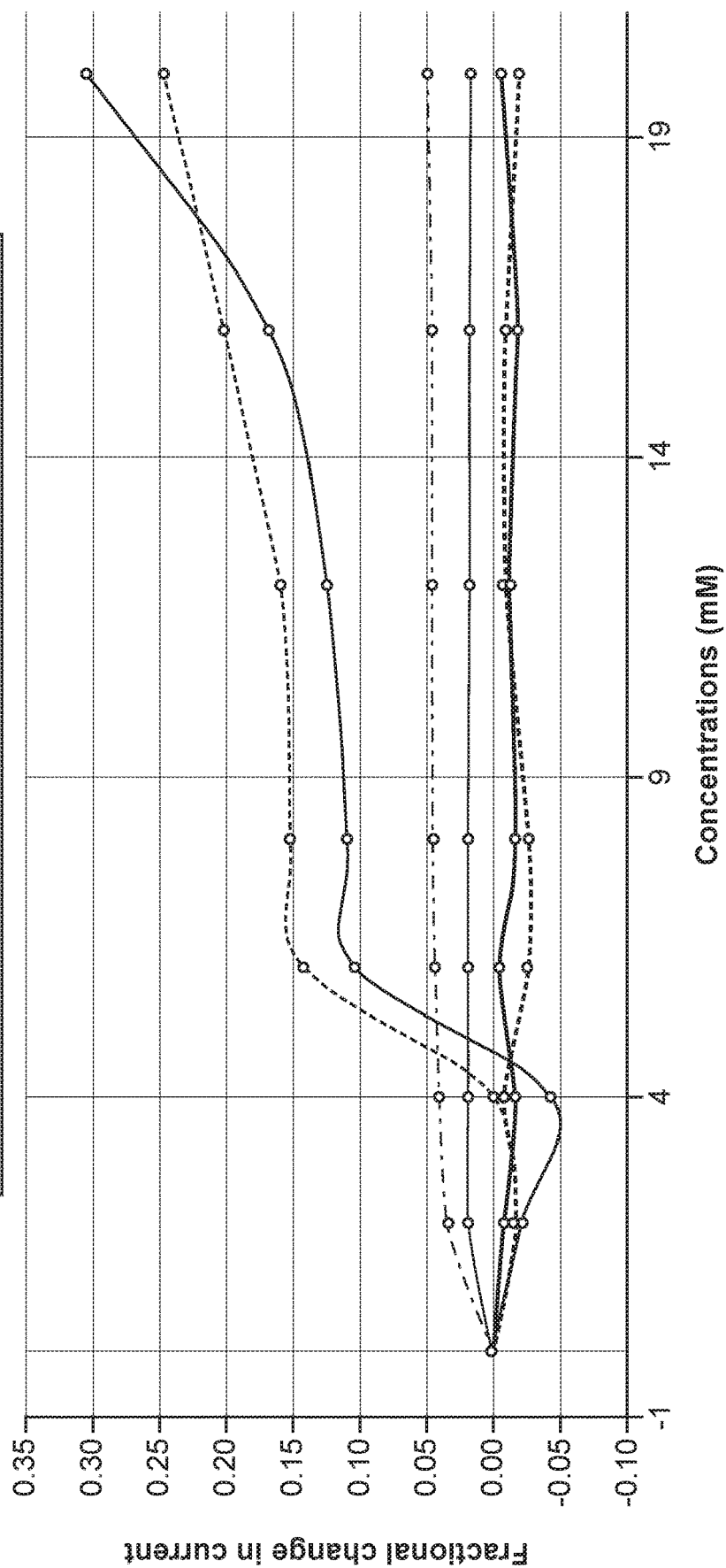
FIG. 18 illustrates an exemplary embodiment, showing selectivity measurements of lactic acid response in various solutions.

FIG. 18 shows that the GFET gave no significant response to just NaCl or NaCl-Glucose control and a polynomial response to increasing lactic acid concentrations in NaCl and NaCl-Glucose solution. The increasing concentrations changed the voltage across the channel, thereby showing high selectivity towards lactic acid. There was no significant response on the non-functionalized sensor for the lactic acid NaCl solution, further emphasizing on the selectivity and sensitivity of the sensor towards lactic acid.

Lactic Acid Response in NaCl Vs. Lactic Acid Response in DI Water:

Response of various lactic acid concentrations in DI water and NaCl solutions were measured on the GFET to study the sensitivity of the functionalized sensor towards lactic acid in DI water vs. lactic acid in NaCl and to understand the effect of NaCl solutions. Solutions with varying concentrations of lactic acid, ranging from 0.1 to 100 mg/dL, in DI water and NaCl, respectively, were prepared. The test started with introducing 2 ul of the lowest concentrations on the GFET followed by the next higher concentration after 3 minutes and so on. This was continued until all the concentrations were introduced onto the GFET.

Figure 19:
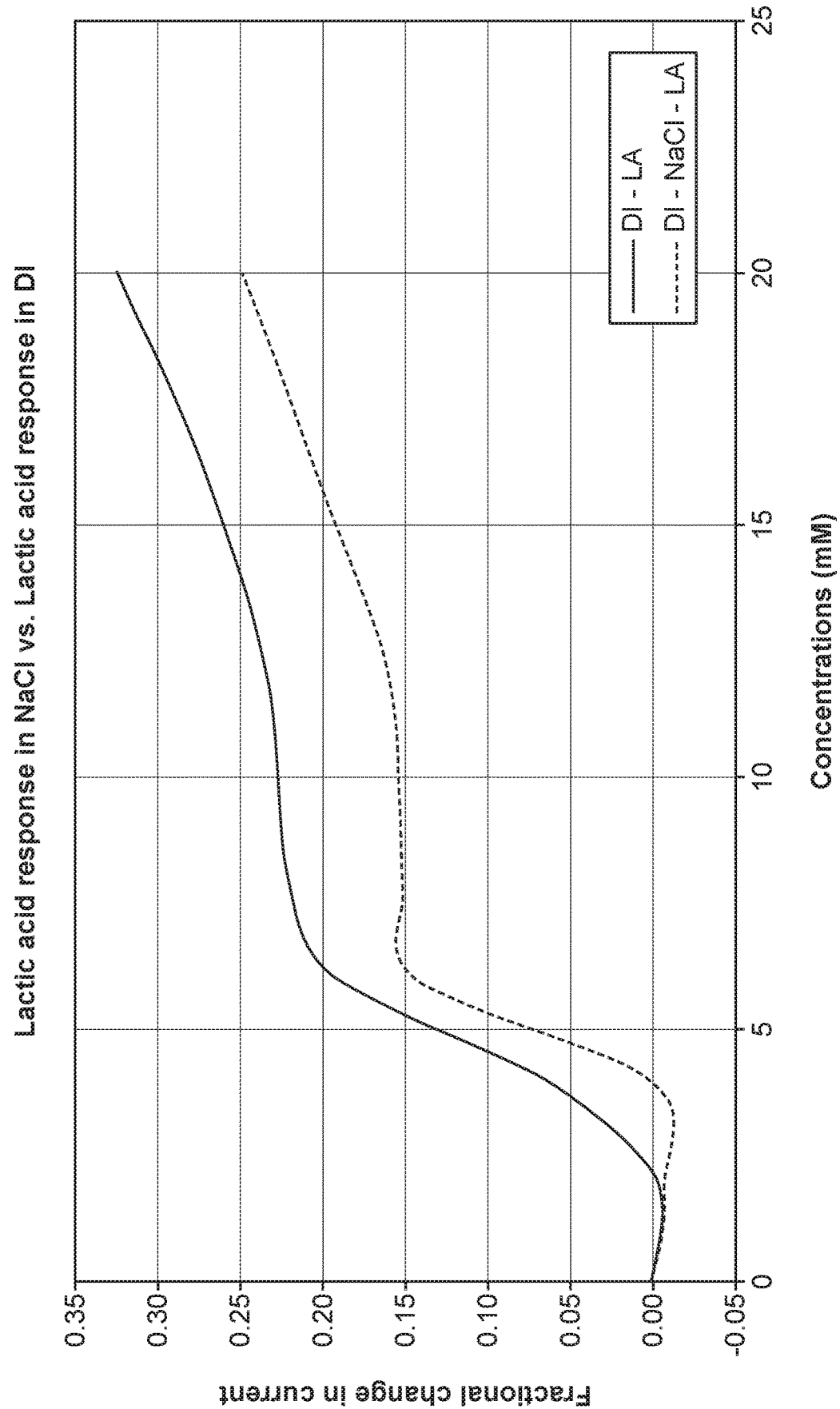
FIG. 19 illustrates an exemplary embodiment, showing lactic acid response in NaCl vs lactic acid response in DI water.

FIG. 19 shows that the lactic acid response in NaCl is less amplified than lactic acid response in DI water.

Figure 20:
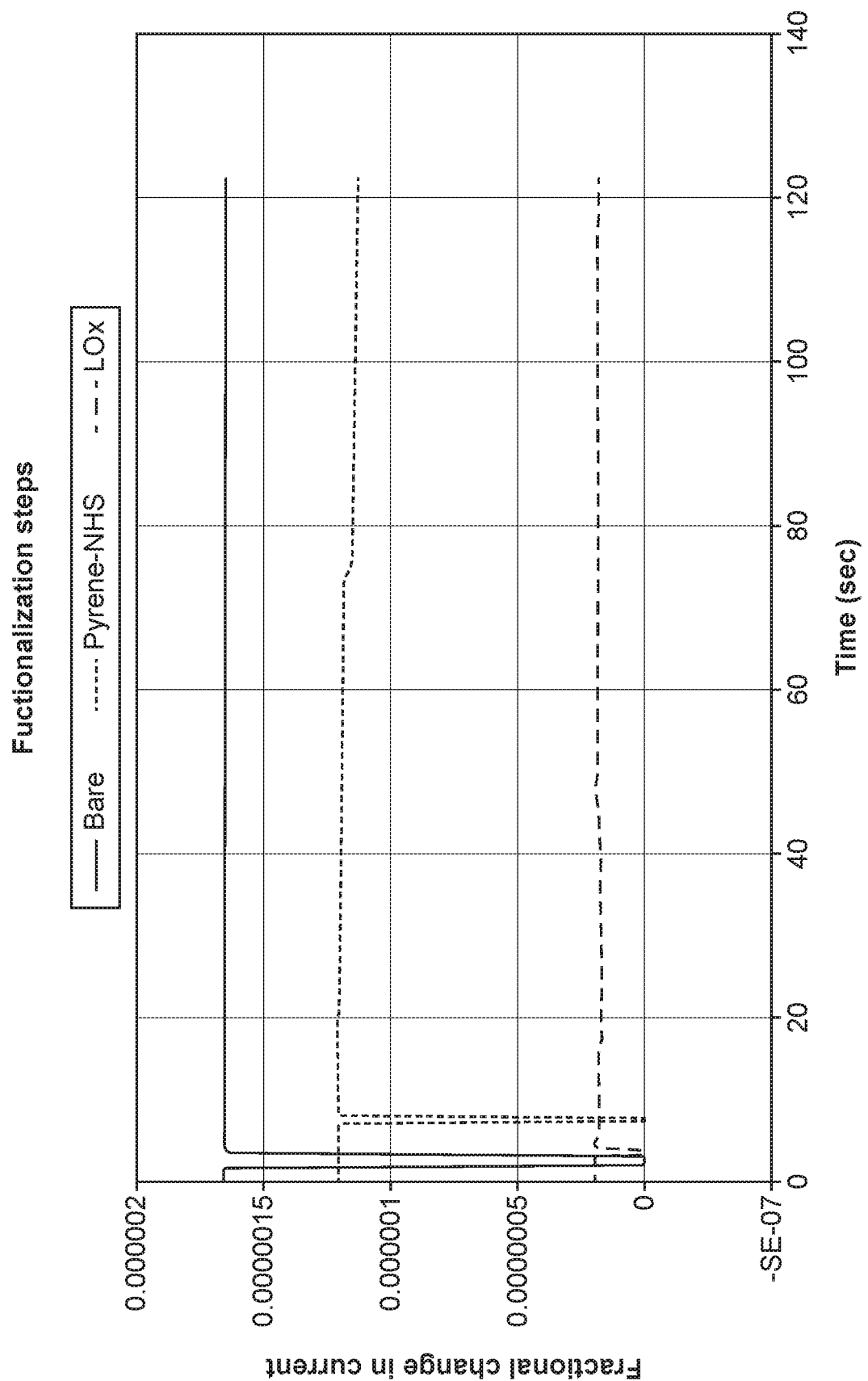
FIG. 20 illustrates an exemplary embodiment, showing lactic acid functionalization steps visualized through the GFET fabrication.

Lactic Acid Functionalization Steps Visualized Through the GFET Fabrication:

The current responses for graphene sensor, before functionalization, after functionalization and after lactic acid is introduced on the sensor are depicted in FIG. 20. This helps in understanding each stage of the GFET fabrication step and how after each stage the current response of the GFET changes. For example, FIG. 20 shows that the current response decreases after functionalization (orange) as compared to before functionalization (blue). The linker molecule attracts the lactic acid molecules and binds to it thereby reducing the current on the GFET as compared to its previous state.

The following novel results and/or features were observed.

High Selectivity:

The GFETs (NFETs) functionalized with LOx gave a highly selective response (>94%) to Lactic concentrations in different control fluids.

High Sensitivity:

The GFETs functionalized with Pyrene NHS exhibited a high sensitivity for lactic acid with a limit of detection (LOD) of 250 femto gram/litre; i.e., 2.78e-'2 mmol/l. The existing lactic acid meters have an LOD between 0.001-10 mmol/l. The The GFET functionalized with Pyrene NHS is approx. 108 times sensitive than the existing standard lactic acid measurement devices. The GFET sensors have a high signal to noise ratio, are highly selective and due to the high surface area for bonding there is higher bonding between the surface and the receptor molecules. All these factors play a huge differentiating role in making GFETs highly sensitive.

Gate Modulation Due to Polar Molecules:

In polar fluids (like water, salt etc.) it was observed that the polar molecules (such as ions) formed a polar fluid gate terminal (PFGT) on the NFETs. The polar molecules near the graphene surface induced a dielectric effect creating a channel for charge transfer. The gating strength of the PFGT was dependent both the charge and concentration of the polar molecules in the fluid. Such a third polar fluid gate terminal (PFGT) modulated the electrical responses from the lactic acid concentrations in a polar fluid.

Induced Motion of the of the Polar Fluid Over Surface of NFET:

It was observed that the polar fluid (like lactic acid in artificial sweat) would try to immediately repel or come off from the NFET surface, due to increased hydrophobicity between NFET surface and the polar fluid. The higher the concentration of the polar molecules in the fluid, more the strength of the PFGT and hence more the repelling effect. This repelling effect combined with the modulation of the electrical response due to the PFGT on the NFET allowed for a highly sensitive, selective and continuous monitoring lactic acid system.

Example 5

Additional Analyses

Figure 21:
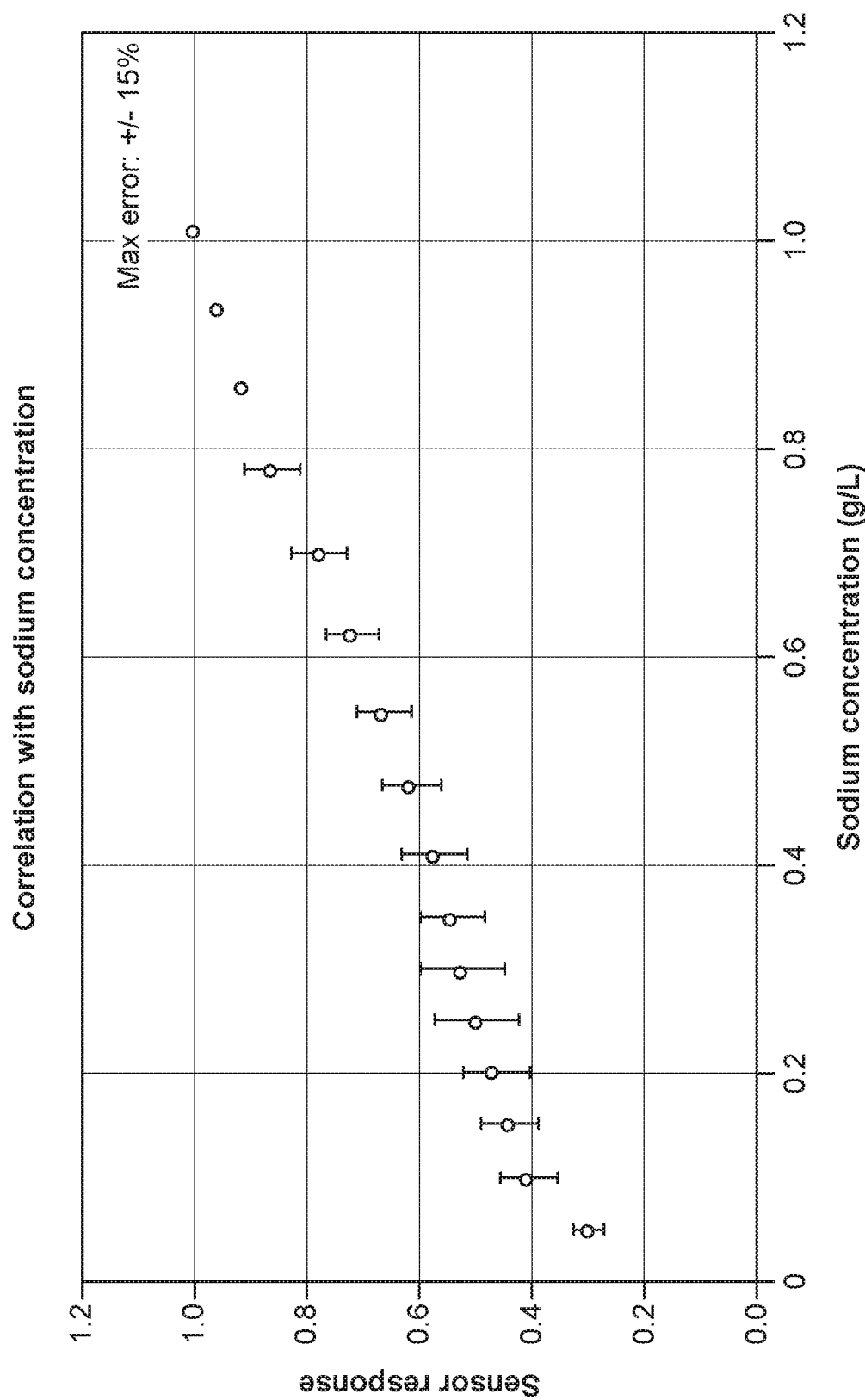
FIG. 21 illustrates an exemplary embodiment, showing a model for sensor correlation with sweat sodium concentration.

Sweat Salt Concentration Correlation:

FIG. 21 represents, the sweat sensor response for a corresponding sweat sodium concentration.

Increasing concentrations of NaCl (0.1 mg/dl to 100 mg/dl) were added on the graphene sensor, every 3 minutes. The test started with dropping 2 ul of the lowest concentration (e.g., 0.1 mg/dl) followed by the next higher concentration (e.g., 0.2 mg/dl) and so on with an interval of 3 minutes. Corresponding fractional change in voltage was measured. This was repeated for 10 different sensors and a max error of 15% was observed. This acts as a model for correlation between sweat sodium and corresponding change in voltage.

Figure 22:
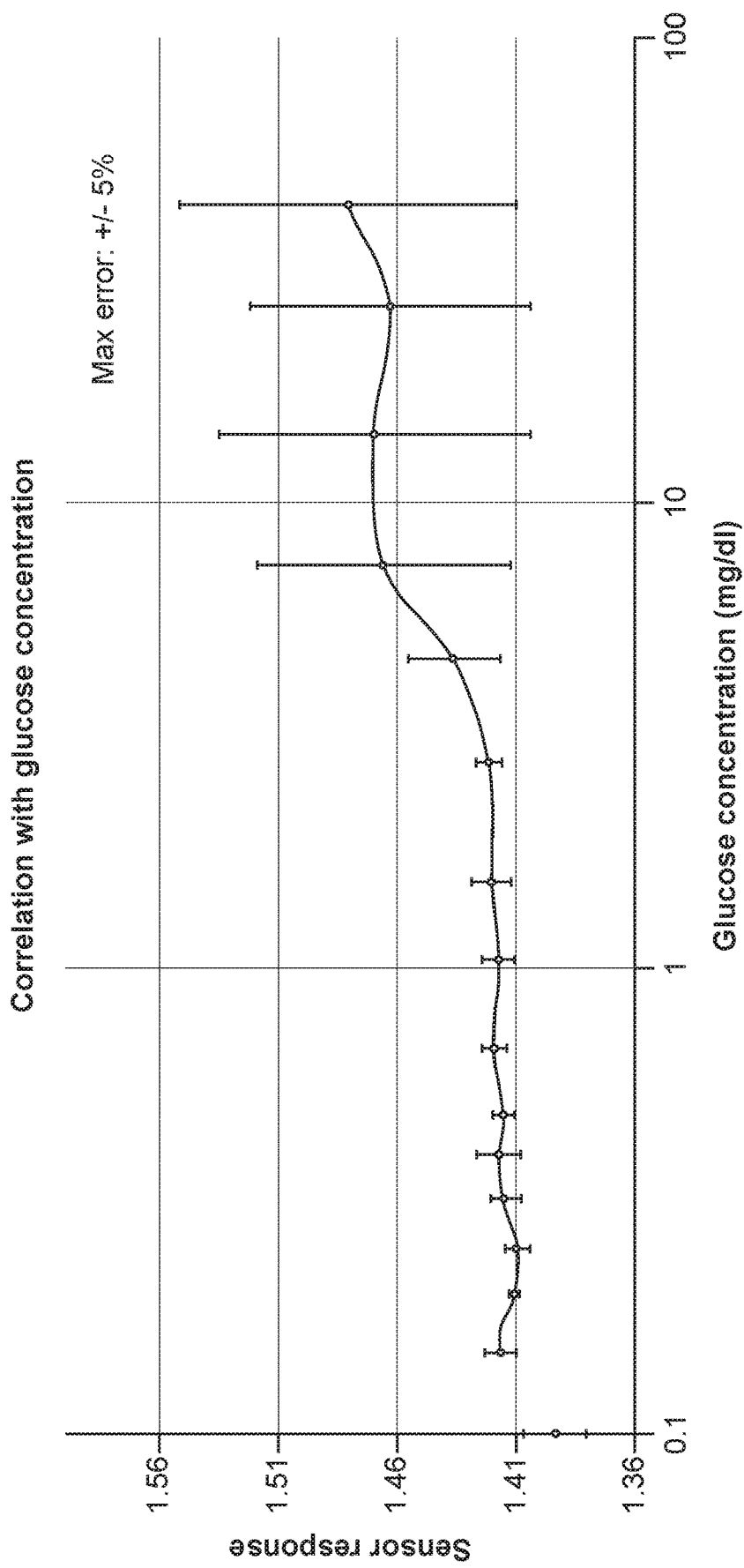
FIG. 22 illustrates an exemplary embodiment, showing a model for sensor correlation with sweat glucose concentration.

Sweat Glucose Concentration Correlation:

FIG. 22 represents, the sweat sensor response for a corresponding sweat glucose concentration.

Increasing concentrations of glucose (0.1 mg/dl to 100 mg/dl) were added on the graphene sensor, every 3 minutes. The test started with dropping 5 ul of the lowest concentration (e.g., 0.1 mg/dl) followed by the next higher concentration (e.g., 0.2 mg/dl) and so on with an interval of 3 minutes and corresponding fractional change in voltage was measured. This was repeated for 10 different sensors and a max error of 5% was observed. This acts as a model for correlation between sweat glucose and corresponding change in voltage.

Figure 23:
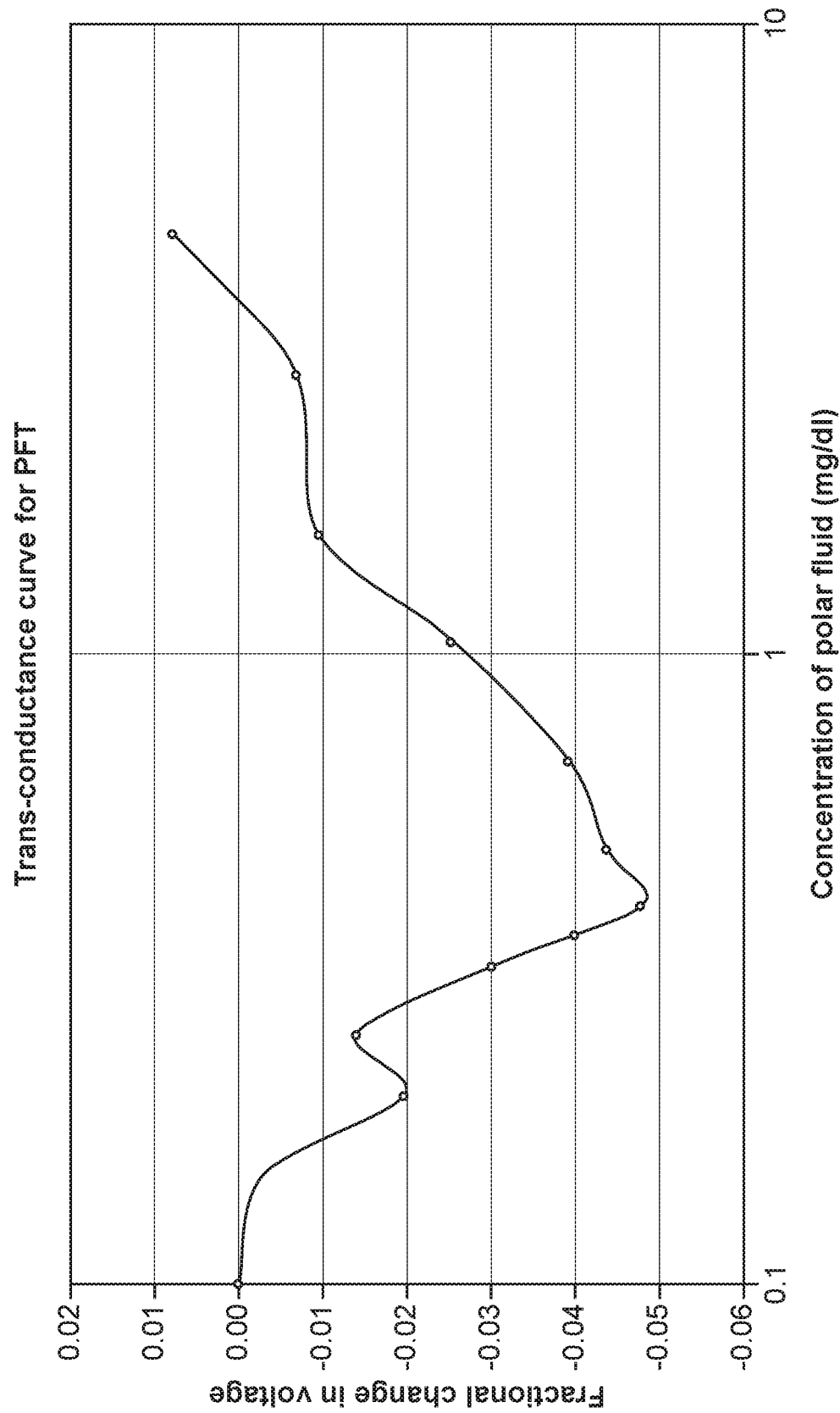
FIG. 23 illustrates an exemplary embodiment, showing a trans-conductance curve for PFT.

Trans-Conductance Curve:

FIG. 23 represents a trans-conductance curve for the PFGT device.

NaCl solution with increasing concentrations ranging from 0.1 ng/dl to 1 mg/dl is dropped every 3 minutes on the sensor. The test starts with dropping 2 ul of the lowest concentration (e.g., 0.1 ng/dl) followed by the next higher concentration (1 ng/dl) and so on with an interval of 3 minutes.

As the polar fluid is introduced, a debye layer is formed on the graphene sensor and a gating effect is observed, both the debye length and the gating effect are a function of the concentration of the polar molecules. For the initial concentrations of NaCl solution, DI is more dominant, due to which more holes are created and we see a drop in the voltage. However, after a few drops, when the concentration of the NaCl increasing in the solution, it becomes more dominant and more electrons are created near the debye layer, thereby showing an increase in the voltage.

This shows the trans-conductance characteristic of the graphene sensor gated with a polar fluid.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A biosensing system comprising:
   a sensor comprising:
   a multi-terminal structure on a substrate, wherein the multi-terminal structure comprises a nanoscale material layer arranged on the substrate as a channel connecting at least two terminals of the multi-terminal structure,
   wherein a polar fluid induced gate terminal is created when a polar fluid interacts with a surface of the channel, and wherein a gate voltage is induced by the polar fluid thereby transforming the multi-terminal structure into an active device, wherein the biosensing system is wearable, wherein the nanoscale material layer is configured to be in proximity to a subject, and wherein the polar fluid comprises a fluid released from the subject; and
   a detector comprising:
   a digital platform configured to receive a voltage output or a current output from the multi-terminal structure, wherein the voltage output or the current output is associated with a concentration of one more target analytes in the polar fluid.

2. The biosensing system of claim 1, wherein the at least two terminals comprises at least one source terminal and at least one drain terminal.

3. The biosensing system of claim 2, wherein the channel is formed connecting between the at least one source terminal and the at least one drain terminal.

4. The biosensing system of claim 1, wherein the polar fluid is externally introduced onto the channel as a droplet.

5. The biosensing system of claim 1, wherein the polar fluid is externally introduced onto the channel when the multi-terminal structure comes into contact with a volume of the polar fluid or is immersed in the volume of the polar fluid or both.

6. The biosensing system of claim 1, wherein the multi-terminal structure does not comprise or require a permanent physical gate terminal to be formed on the substrate.

7. The biosensing system of claim 1, wherein the gate voltage is associated with a concentration of charged particles within the polar fluid.

8. The biosensing system of claim 1, wherein the polar fluid and the channel collectively function as the polar fluid induced gate terminal in the multi-terminal structure.

9. The biosensing system of claim 1, wherein the polar fluid induced gate terminal is transient and active only when the polar fluid is externally introduced onto the channel.

10. The biosensing system of claim 1, wherein the multi-terminal structure is not capable of functioning as the active device when the polar fluid is removed from the channel.

11. The biosensing system of claim 1, wherein the channel is electrically conductive, and chemically or biologically sensitive or both chemically and biologically sensitive.

12. The biosensing system of claim 1, wherein the nanoscale material layer is grown epitaxially and transferred onto the substrate using wet or dry deposition methods.

13. The biosensing system of claim 1, wherein the nanoscale material comprises graphene, CNTs, $MoS_2$, boron nitride, metal dichalcogenides, phosphorene, nanoparticles, quantum dots, fullerene, 2D nanoscale material, 3D nanoscale material, 0D nanoscale material, 1D nanoscale material, or any combination thereof.

14. The biosensing system of claim 1, further comprising:
   a receptor layer coupled to the nanoscale material layer, wherein the receptor layer comprises one or more receptors configured to target one or more target analytes in the polar fluid.

15. The biosensing system of claim 14, wherein the one or more receptors comprises pyrene boronic acid (PBA), pyrene N-hydroxysuccinimide ester (Pyrene-NHS), organic chemicals, aromatic molecules, cyclic molecules, enzymes, proteins, antibodies, viruses, single stranded DNAs (ssDNAs), aptamers, inorganic materials, synthetic molecules, or biological molecules.

16. The biosensing system of claim 1, further comprising:
   a back polymer layer coupled to the nanoscale material layer, wherein the back polymer layer is configured to provide support for additional mechanical, electrical, chemical, biological functionality, or combinations thereof.

17. The biosensing system of claim 16, wherein the back polymer layer comprises carbon polymers, bio polymers, PMMA, PDMS, flexible glass, nanoscale materials, silica gel, silicone, inks, printed polymers, or any combination thereof.

18. The biosensing system of claim 1, wherein the substrate comprises polyimide, flexible printed circuits (FPC), polyamide, polyurethane, PET, PDMS, PMMA, silicon dioxide, silicon, glass, aluminum oxide, sapphire, germanium, gallium arsenide, indium phosphide, an alloy of silicon and germanium, fabrics, textiles, silk, paper, cellulose based materials, or any combination thereof.

19. The biosensing system of claim 1, wherein the substrate is made of an electrically insulating material.

20. The biosensing system of claim 1, wherein the nanoscale material layer is configured to contact a skin of a subject, and wherein the fluid released from the subject comprises a fluid released from the skin of the subject.

21. The biosensing system of claim 1, wherein the polar fluid comprises a solution or a gas comprising containing polar molecules.

22. The biosensing system of claim 1, wherein the polar fluid comprises sweat, breath, saliva, earwax, urine, semen, blood plasma, a bio-fluid, a chemical fluid, an air sample, a gas sample, or a combination thereof.

23. The biosensing system of claim 1, wherein the polar fluid comprises one or more target analytes comprising an electrolyte, glucose, lactic acid, IL6, a cytokine, HER2, cortisol, ZAG, cholesterol, vitamins, a protein, a drug molecule, a metabolite, a peptide, an amino acid, a DNA, an RNA, an aptamer, an enzyme, a biomolecule, a chemical molecule, a synthetic molecule, or combinations thereof.

24. The biosensing system of claim 1, wherein the digital platform is configured to receive the voltage output or the current output through a wired or a wireless transmission.

25. The biosensing system of claim 1, wherein the digital platform comprises one or more of a smart phone, a tablet computer, a smart watch, an in-car entertainment system, a laptop computer, desktop computers, a computer terminal, a television system, a wearable device, or an e-book reader.

* * * * *